United States Patent [19]

Leonardi et al.

[11] Patent Number: 5,990,114
[45] Date of Patent: Nov. 23, 1999

[54] USE OF 5-HT$_{1A}$ RECEPTOR ANTAGONISTS FOR THE TREATMENT OF URINARY INCONTINENCE

[75] Inventors: Amedeo Leonardi; Rodolfo Testa, both of Milan, Italy

[73] Assignee: Recordati, S.A., Chemical and Pharmaceutical Company, Chiasso, Switzerland

[21] Appl. No.: 08/807,338

[22] Filed: Feb. 28, 1997

Related U.S. Application Data

[60] Provisional application No. 60/023,246, Aug. 12, 1996.

[30] Foreign Application Priority Data

Feb. 28, 1996 [IT] Italy .................. MI96A0378

[51] Int. Cl.$^6$ .................................................. A61K 31/495
[52] U.S. Cl. .......................................................... 514/255
[58] Field of Search ............................................ 514/255

[56] References Cited

U.S. PATENT DOCUMENTS

| | | |
|---|---|---|
| 4,576,959 | 3/1986 | Flaugh . |
| 5,387,593 | 2/1995 | Mattson et al. . |

FOREIGN PATENT DOCUMENTS

| | | | |
|---|---|---|---|
| 395312 | 10/1990 | European Pat. Off. . | |
| 395313 | 10/1990 | European Pat. Off. . | |
| 444854 | 9/1991 | European Pat. Off. . | |
| 481744 | 4/1992 | European Pat. Off. . | |
| 490772 | 6/1992 | European Pat. Off. . | |
| 0 512 755 | 11/1992 | European Pat. Off. | C07D 213/75 |
| 546583 | 6/1993 | European Pat. Off. . | |
| 558245 | 9/1993 | European Pat. Off. . | |
| 574313 | 12/1993 | European Pat. Off. . | |
| 590971 | 4/1994 | European Pat. Off. . | |
| 633260 | 1/1995 | European Pat. Off. . | |
| 2255337 | 11/1992 | United Kingdom . | |
| 2262093 | 6/1993 | United Kingdom . | |
| 2277517 | 11/1994 | United Kingdom . | |
| WO 93/07135 | 4/1993 | WIPO . | |
| WO 94/03444 | 2/1994 | WIPO . | |
| WO 94/15919 | 7/1994 | WIPO . | |
| WO 94/15928 | 7/1994 | WIPO . | |
| WO 94/20481 | 9/1994 | WIPO . | |
| WO 94/21610 | 9/1994 | WIPO . | |
| WO 94/21611 | 9/1994 | WIPO . | |
| WO 95/02592 | 1/1995 | WIPO . | |
| WO 95/11891 | 5/1995 | WIPO . | |
| WO 93/33743 | 12/1995 | WIPO . | |
| WO 95/33743 | 12/1995 | WIPO . | |
| WO 96/05817 | 2/1996 | WIPO . | |
| 97/00897 | 2/1997 | WIPO . | |

OTHER PUBLICATIONS

Database Chemical Abstracts on STN, AN 1993:521179, "Effects of Serotonergic agonists on micturition and sexual function in the rat", Drug Dev. Res. (1992), 27(4), 361–75, Jan. 1992.

Chemical Abstracts AN 1996:428601, Oquiza et al, EP 714663, Nov. 1995.
Chemical Abstracts AN 1993:169115, Cliff et al, EP 512755 A2, Apr. 30, 1992.
Alexander, B.S. et al., *J. Pharm. Pharmacol.* 40, 888 (1988).
Andersson, *Drugs* 35:477 (1988).
Bertin B. et al., *J. Biol. Chem.* 267:8200 (1992).
Bliss, *Quart. J. Pharm. Pharmacol.,* 11:192 (1938).
Cheung, Y–D. et al., *Eur. J. Pharmacol.* 84, 79 (1982).
Creese, I. et al., *Eur J. Pharmacol.* 60, 55 (1979).
D. Dauzonne et al., *Synthesis,* 348 1984.
De Groat, *Neurobiology of Incontinence,* (Ciba Foundation Symposium 151:27, (1990).
Dray, *J. Pharmacol. Methods,* 13:157 (1985).
Fletcher et al., *Eur. J. Pharmacol.* 237:283 (1993).
Fletcher et al., *TIPS* 14:441 (1993).
Greene, T.W., Chapter 7 "Protective Groups in Organic Synthesis", John Wiley and Sons, New York (1981).
Guarneri, L. (*Pharmacol. Res.,* 27(2):173(1993).
Guarneri, L. et al., *Drugs of Today* 30(2):91 (1994).
Guarneri, L. et al., *Pharmacol. Res.,* 24:175 (1991).
Guarneri, L. et al., XXVII Congresso Naxionale Della Societa Italiana Di Farmacologia, 1994, p. 310.
Hanft, G. et al., *J. Pharm. Pharmacol.* 41, 714 (1989).
Lecci, K. et al., *J. Pharmacol. Exp. Therapeutics* 262:181 (1992).
Lepor, H., *Urology,* 42:483 (1993).
Maggi, C.A. et al., *Brain Res.,* 380:83 (1986).
Maggi, C.A. et al., *Brain Res.,* 415:1 (1987).
Maggi, C.A. et al., *J. Pharmacol. Meth.,* 15:157 (1986).
Maggi, C.A. et al., *J. Urol.,* 136:696 (1986).
Maggi, C.A. et al., *Naun. Schmied. Arc.Pharmacol.,* 332:276 (1986).
Maggi, C.A. et al., *J. Pharmacol. Exp. Ther.,* 230:500 (1984).
Moser, R.C., *Eur. J. Pharmacol.* 193:165 (1991).
Al Neirabeyeh, M. et al.,*Eur. J. Med. Chem.* 26,497 (1991).
Pietra, C. et al., *IRCS Med. Sci.,* 14:992 (1986).
Ruffman, R. *J. Int.Med. Res.* 16:317 (1988).
Saxena, P.R., *Pharmac. Ther.* 66:339 (1995).
Schoefter, R. et al., *Brit. J. Pharmacol.* 95:975 (1988).
Stockmeier, C.A. et al., *Life Sci.,* 38, 117–127 (1966).
Shenker, A. et al., *Eur. J. Pharmacol.* 109:427–429 (1985).
*The RBI Handbook of Receptor Classification,* Kebabian and Nemeyer, Eds., pp. 58–61 (1994), RBI2.
Thorberg, S.O. et al., Acta Pharm. Suec. 24, 169 (1987).
Tricklebank, R.D. et al., *Eur. J. Pharmacol.* 117:15 (1985).
Vandermaelen, C.P. et al., *Brain Res.,* 289:109–119 (1983).
Yaksh, T.K. et al. *Amer. J. Physiol.,* 251:R1177 (1986).

Primary Examiner—Keith D. MacMillan
Attorney, Agent, or Firm—Darby & Darby

[57] ABSTRACT

The present invention discloses compositions and methods for treating neuromuscular dysfunction of the lower urinary tract in mammals, including humans, using serotonin 5-HT$_{1A}$ receptor antagonist compounds that exert their inhibitory effects via pre-synaptic (somatodendritic) and post-synaptic antagonism.

35 Claims, No Drawings

USE OF 5-HT$_{1A}$ RECEPTOR ANTAGONISTS FOR THE TREATMENT OF URINARY INCONTINENCE

This application claims the benefit of the filing date of provisional patent application Serial No. 60/023,246, filed Aug. 12, 1996 under 35 U.S.C. §119, the entire contents of which are incorporated by reference herein in their entirety. This application also claims priority under 35 U.S.C. § 119 from Italian application MI96A 000378.

FIELD OF THE INVENTION

The present invention relates to compositions and methods for treating neuromuscular dysfunction of the lower urinary tract in mammals, including humans, using serotonin 5-HT$_{1A}$ receptor antagonist compounds that exert their inhibitory effects via pre-synaptic (somatodendritic) and post-synaptic antagonism.

BACKGROUND OF THE INVENTION

In mammals, micturition (urination) is a complex process that requires the integrated actions of the bladder, its internal and external sphincters, the musculature of the pelvic floor, and neurological control over these muscles at three levels (in the bladder wall or sphincter itself, in the autonomic centers of the spinal cord, and in the central nervous system at the level of the pontine micturition center (PMC) in the brainstem (pons) under the control of cerebral cortex) (De Groat, *Neurobiology of Incontinence*, (Ciba Foundation Symposium 151:27, 1990). Micturition results from contraction of the detrusor muscle, which consists of interlacing smooth muscle fibers under parasympathetic autonomic control from the sacral spinal cord. A simple voiding reflex is formed by sensory nerves for pain, temperature, and distension that run from the bladder to the sacral cord. However, sensory tracts from the bladder also reach the PMC, resulting in the generation of nerve impulses that normally suppress the sacral spinal reflex arc controlling bladder emptying. Thus, normal micturition is initiated by voluntary suppression of cortical inhibition of the reflex arc and by relaxation of the muscles of the pelvic floor and the external sphincter. Finally, the detrusor muscle contracts and voiding occurs.

Abnormalities of lower urinary tract function, e.g., dysuria, incontinence, and enuresis, are common in the general population. Dysuria includes urinary frequency, nocturia, and urgency, and may be caused by cystitis, prostatitis or benign prostatic hypertrophy (BPH) (which affects about 70% of elderly males), or by neurological disorders. Incontinence syndromes include stress incontinence, urgency incontinence, and overflow incontinence. Enuresis refers to the involuntary passage of urine at night or during sleep.

Prior to the present invention, treatment of neuromuscular dysfunction of the lower urinary tract has involved administration of compounds that act directly on the bladder muscles, such as flavoxate, a spasmolytic drug (Ruffman, *J. Int.Med.Res.* 16:317, 1988) also active on the PMC (Guarneri et al., *Drugs of Today* 30:91, 1994), or anticholinergic compounds such as oxybutynin (Andersson, *Drugs* 35:477, 1988). The use of α1-adrenergic receptor antagonists for the treatment of BPH is also common but is based on a different mechanism of action. (Lepor, *Urology,* 42:483, 1993).

However, treatments that involve direct inhibition of the pelvic musculature (including the detrusor muscle) may have unwanted side effects such as incomplete voiding or accommodation paralysis, tachycardia and dry mouth (Andersson, *Drugs* 35:477, 1988). Thus, it would be preferable to utilize compounds that act via the peripheral or central nervous system to, for example, affect the sacral spinal reflex arc and/or the PMC inhibition pathways in a manner that restores normal functioning of the micturition mechanism.

Lecci et al. (*J. Pharmacol.Exp. Therapeutics* 262:181, 1992) describe the effects of the 5-HT$_{1A}$ receptor ligands 8-hydroxy-2-(di-N-propylamino)tetralin (8-OH-DPAT) and 1-(2-methoxyphenyl)-4-[4-(2-phthalimido)butyl]piperazine (NAN-190, reference Compound Q) on micturition reflexes in the anesthetized rat. 8-OH-DPAT (an agonist) stimulated the supra-spinal micturition reflex (SMR) originating from the PMC, while NAN-190 inhibited the SMR. The authors concluded that spinal and supraspinal 5-HT$_{1A}$ receptors modulate the SMR in this system. The present inventors and their coworkers, however, have found that the efficacy of NAN-190 and other 5-HT$_{1A}$ receptor ligands in inhibiting SMR is directly correlated to their relative binding affinities for the α1 adrenergic receptor, rather than to their affinities, if any, for the 5-HT$_{1A}$ receptor (Guarneri et al., XXVII Congresso Nazionale Della Societa Italiana Di Farmacologia, 1994, page 310), which called into question the relevance of 5-HT$_{1A}$ antagonistic activity for treatment of neuromuscular dysfunction of the lower urinary tract. Furthermore, since NAN-190 is considered a partial 5-HT$_{1A}$ receptor agonist rather than a complete or "true" antagonist, there was no basis for concluding that "true" 5-HT$_{1A}$ receptor antagonism would be important for treating neuromuscular dysfunction of the lower urinary tract. The present inventors postulated that coordinated pre-synaptic and post-synaptic 5-HT$_{1A}$ receptor antagonism (see below) is an effective means to treat urinary tract disorders.

Many classes of 5-HT receptors have been identified, including 5-HT$_1$, 5-HT$_2$, 5-HT$_3$, and 5-HT$_4$. 5-HT$_1$ receptors further comprise 5-HT$_{1A}$, 5-HT$_{1B}$, 5-HT$_{1D}$, 5-HT$_{1E}$, and 5-HT$_{1F}$ subtypes, and 5-HT$_2$ receptors comprise 5-HT$_{2A}$, 5-HT$_{2B}$, and 5-HT$_{2C}$ subtypes (*The RBI Handbook of Receptor Classification*, Kebabian and Nemeyer, Eds., page 58–61 (1994), RBI). Additional related receptor families include 5-HT$_{5A}$, 5-HT$_{5B}$, 5-HT$_6$ and 5-HT$_7$ (Saxena, *Pharmac. Ther.* 66:339, (1995)).

With respect to the 5-HT$_{1A}$ receptor, at least two functionally distinct types of this receptor subtype have been identified, which are designated "pre-synaptic" (or somatodendritic) and "post-synaptic". Pre-synaptic receptors are present on 5-HT-producing neurons and are involved in autoregulation of 5-HT release; their activation causes physiological changes including hyperphagia, hypothermia (in the mouse), bradycardia and hypotension. Post-synaptic receptors are widely distributed throughout the mammalian brain and are coupled to potassium channels and adenylate cyclase; their activation leads to "5-HT behavioral syndrome", hypothermia (in the rat), and elevation of plasma corticotropin levels. Beyond the differences in their anatomical distribution and functioning, pre-synaptic and post-synaptic receptors can be distinguished by the differential activity profiles of different 5-HT$_{1A}$ receptor ligands. For example, full agonists such as 8-OH-DPAT and 5-carboxytryptamine have agonist activity on both pre-synaptic and post-synaptic receptors. By contrast, partial agonists such as buspirone, ipsapirone, spiroxantine, urapidil, NAN-190, and BMY 7378 have agonist activity on pre-synaptic receptors and antagonist activity on post-synaptic receptors. Finally, compounds such as those encompassed by the present invention, referred to as "true" 5-HT$_{1A}$ receptor antagonists, exhibit antagonistic activity on both pre-synaptic and post-synaptic receptors.

SUMMARY OF THE INVENTION

It has now been unexpectedly found that 5-HT$_{1A}$ receptor antagonist compounds are useful in the treatment of neuromuscular dysfunction of the lower urinary tract in mammals. Useful compounds act as effective 5-HT antagonists at both pre-synaptic and post-synaptic 5-HT$_{1A}$ receptors.

Thus, the present invention provides methods for treating neuromuscular dysfunction of the lower urinary tract in mammals, including without limitation dysuria, incontinence, and enuresis. The methods involve administering to affected mammals effective amounts for treating the disorders of compounds within the foregoing class, preferably having the following structures:

1) Piperazine Derivatives Having General Formula I (I)

wherein:

Ra is selected from the group consisting of hydrogen, and lower alkyl;

Ra$^1$ is selected from the group consisting of aryl, nitrogen-containing heteroaryl, and bicyclic heteroaryl; and Xa is selected from the group consisting of (Aa)

(Ba)

(Ca)

(Da)

and (Ea)

wherein na is 1 or 2; ma is 1, 2, or 3;

Ra$^2$ and Ra$^4$ are independently selected from the group consisting of hydrogen and lower alkyl;

Ra$^3$ is selected from the group consisting of aryl and aryl(lower)alkyl;

Ra$^5$ is selected from the group consisting of hydrogen, lower alkyl, cycloalkyl, and cycloalkyl(lower)alkyl; or Ra$^4$ and Ra$^5$ taken together with the nitrogen atom to which they are attached can form, a ring, such as, for example, an azetidino, pyrrolidino, piperidino, hexahydroazepino, morpholino, or piperazino ring; said ring can optionally be substituted by lower alkyl, aryl, or aryl(lower)alkyl.

Ka is a C$_2$–C$_4$ alkylene chain which can be optionally substituted by one or more lower alkyl groups;

Ra$^6$ is selected from the group consisting of a monocyclic heteroaryl radical and a bicyclic heteroaryl radical;

Ra$^7$ is selected from the group consisting of hydrogen, lower alkyl, cycloalkyl, cycloalkenyl, cycloalkyl(lower)alkyl, aryl, aryl(lower)alkyl, heteroaryl, heteroaryl(lower)alkyl, —NRa$^8$Ra$^9$, and —O—Ra$^{10}$;

wherein Ra$^8$ is selected from the group consisting of hydrogen, lower alkyl, aryl, and aryl(lower)alkyl;

Ra$^9$ is selected from the group consisting of hydrogen, lower alkyl, —CO—(lower)alkyl, aryl, —CO—aryl, aryl (lower)alkyl, cycloalkyl, and cycloalkyl(lower)alkyl; or Ra$^8$ and Ra$^9$ taken together with the nitrogen atom to which they are attached can form a saturated heterocyclic ring which optionally contains additional hetero atoms; and Ra$^{10}$ is selected from the group consisting of lower alkyl, cycloalkyl, cycloalkyl(lower)alkyl, aryl, aryl(lower)alkyl, heteroaryl, and heteroaryl(lower)alkyl;

Ra$^{11}$ is selected from the group consisting of aryl, and heteroaryl containing at least one nitrogen atom; and Ra$^{12}$ is hydrogen or lower alkyl;

Ra$^{13}$ is hydrogen, lower alkyl, cycloalkyl or cycloakyl (lower)alkyl; and

Ra$^{14}$ is aryl.

Ya is selected from the group consisting of carbonyl, alkylene, hydroxymethylene, hydroxyalkylene, hydroxycycloalkylene, and —S(O)$_{na}$; where na=0–2. In addition, the Ya groups can be unsaturated, having one or more multiple bonds, or saturated.

Preferred compounds having general Formula I include without limitation

-continued

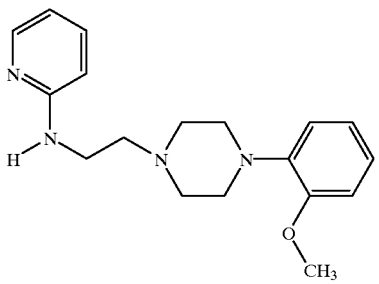

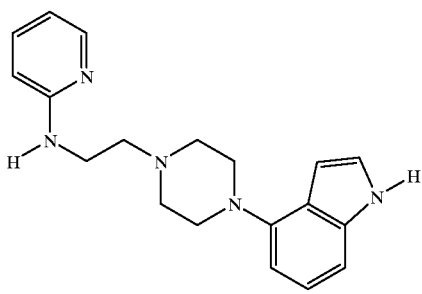

2) Compounds Having General Formula II

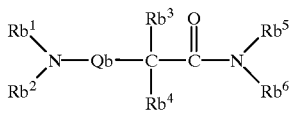
(II)

wherein

Qb represents a $C_{1-3}$ alkylene chain, optionally substituted by one or more lower alkyl groups;

$Rb^1$, $Rb^3$, and $Rb^5$, are independently selected from the group consisting of hydrogen, and lower alkyl; wherein $Rb^1$ and $Rb^2$ can be taken together to form a ring;

$Rb^4$ is aryl, bicyclic aryl, or heteroaryl;

$Rb^6$ is selected from the group consisting of hydrogen, $C_{1-10}$ alkyl, $C_{3-12}$ cycloalkyl, cycloalkyl(lower)alkyl, aryl or aryl(lower)alkyl;

wherein $Rb^5$ and $Rb^6$ can optionally be taken together with the nitrogen atom to which they are attached to form a saturated heterocyclic ring. Said ring can optionally contain an additional hetero atom to form, for example, an azetidino, pyrrolidino, piperidino, hexahydroazepino, morpholino, heptamethyleneimino, or piperazino ring; furthermore, said ring can optionally be substituted by, for example, lower alkyl, aryl, aryl(lower)alkyl, lower alkoxy, halogen or halo(lower)alkyl.

$Rb^2$ represents a group Ab, Bb, Cb, Db, Eb, or Fb, having the formulas:

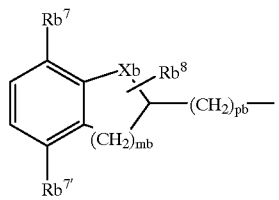
(Ab)

wherein Xb is selected from the group consisting of —$(CH_2)_{nb}$—, —$OCH_2$—, and —$SCH_2$—, mb is 0 or 1, nb is 1, 2, or 3, and pb is 0 or 1; provided that the sum of mb and pb is 1; and that the sum of mb and nb is 1, 2, or 3;

$Rb^7$ is selected from the group consisting of hydrogen, lower alkyl, lower alkoxy, hydroxy, halogen, trifluoromethyl, (lower)alkoxycarbonyl, carboxamido, nitro, cyano, amino, (lower)alkylamino, di(lower)alkylamino, and (lower)alkylcarbonyl;

$Rb^7$ is selected from the group consisting of hydrogen and halogen; with the proviso that when Xb is —$(CH_2)_{nb}$—, and $Rb^{7'}$ is hydrogen or halogen and when Xb is either —$OCH_2$—, or —$SCH_2$—, then —$Rb^{7'}$ is hydrogen.

$Rb^8$ is hydrogen or lower alkyl; or

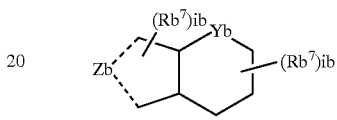
(Bb)

wherein Yb is selected from the group consisting of —O—, —S—, and —$CH_2$—;

Zb represents the atoms necessary to form a heteroaromatic ring, having from 5 to about 7 carbon atoms, fused to the non-aromatic ring containing the Yb group; and wherein each $Rb^7$ group, attached to the heteroaromatic ring or the non-aromatic ring, independently represents one of the groups defined above; and each ib is independently 0, 1, or 2; or $Rb^9$—$CH_2CH_2$— (Cb)

wherein $Rb^9$ represents a monocyclic or bicyclic heteroaryl group; or

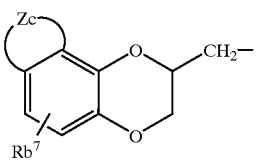
(Db)

where $Rb^7$ is as defined above; and

Zc represents an optional fused aromatic or heteroaromatic ring, or if absent, hydrogen atoms; or $Rb^{10}$—O—$CH_2CH(OH)CH_2$—; or (Eb)

$Rb^{10}$—O—$CH_2CH_2$— (Fb)

where $Rb^{10}$ is selected from the group consisting of aryl, bicyclic aryl, and bicyclic heteroaryl.

The group

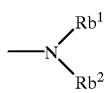

can represent the group

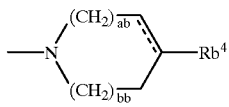

wherein ab and bb each independently represent 0, 1, 2, or 3 with the proviso that the sum of ab and bb is 0, 1, 2, or 3;
$Rb^4$ is as defined above; and
- - - - represents an optional double bond which can be present in the ring; provided that ab is at least 1.

3) Compounds Having General Formula III

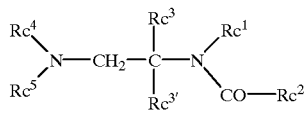

(III)

wherein
$Rc^1$ represents a heteroaryl radical, or a bicyclic heteroaryl radical;
$Rc^2$ is cycloalkyl;
$Rc^3$, $Rc^{3'}$ and $Rc^4$ are each independently selected from the group consisting of hydrogen, and lower alkyl; and
$Rc^5$ is a group having the formula (Ab), (Bb), (Cb), (Db), (Eb), or (Fb) as defined above.

The group

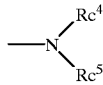

can represent the group

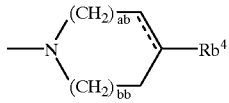

wherein ab, bb, and $Rb^4$ are as defined above, and - - - - represents a single or double bond; with the proviso that $Rb^4$ is not unsubstituted phenyl.

4) Compounds Having General Formula IV

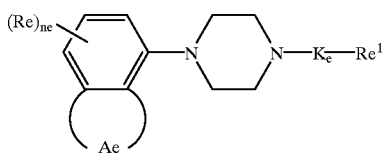

(IV)

wherein
Ae is selected from the group consisting of —OCH=CH—, —OCH$_2$CH$_2$—, —O(CH$_2$)$_{ne}$O—, —OCOCH=CH—; wherein ne is 1 or 2;

Each Re is independently selected from the group consisting of hydrogen, halogen, alkyl, hydroxy, alkoxy, trifluoromethyl, and cyano;

Ke is a linear or branched alkyl group having from 1 to 8 carbon atoms optionally substituted with an (hetero)aryl group;

$Re^1$ is selected from the group consisting of phenyl, thienyl, naphthyl, benzothiophenyl,

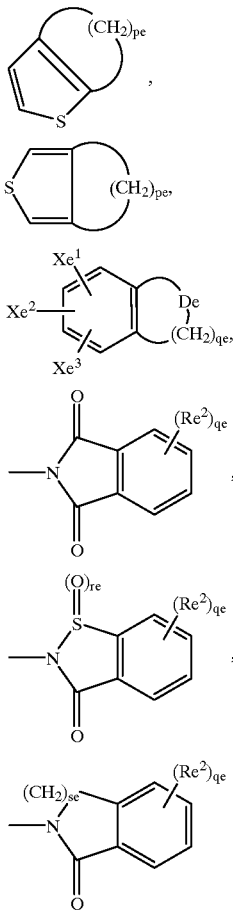

, and wherein pe is 3 or 4;

wherein each $Re^2$ is independently selected from the group consisting of halogen, alkyl, hydroxy, alkoxy, trifluoromethyl, and cyano; and qe is 0 to 3; re is 0 to 2; and se is 1 or 2.

De is selected from the group consisting of —CH=CH—, and (CH$_2$)$_{2-4}$;

$Xe^1$, $Xe^2$, and $Xe^3$ are independently selected from the group consisting of hydrogen, alkyl, alkoxy, hydroxy, alkylthio, —CF$_3$, —NO$_2$, —NH$_2$, and —NHCOCH$_3$, or two of $Xe^1$, $Xe^2$, and $Xe^3$ can be taken together to form an —OCH$_2$O— or —O(CH$_2$)$_2$O— bridge.

5) Compounds Having General Formula V

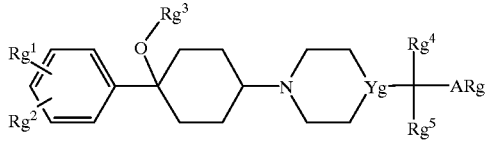
(V)

wherein $Rg^1$ and $Rg^2$ are independently selected from the group consisting of hydrogen, halogen, $CF_3$, and lower alkoxy; or when $Rg^1$ and $Rg^2$ are on adjacent carbon atoms, taken together, they can form an —O(CH$_2$)$_{ig}$O— bridge; wherein ig is from 1 to about 3; with the proviso that $Rg^1$ and $Rg^2$ cannot both be hydrogen.

$Rg^3$, $Rg^4$, and $Rg^5$ are independently selected from the group consisting of hydrogen, lower alkyl, and phenyl;

Yg is N or CH, and

ARg is selected from the group consisting of heteroaryl, substituted phenyl, and unsubstituted phenyl.

The ARg substituted phenyl groups have the formula Ag:

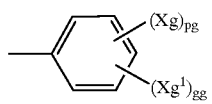
(Ag)

wherein Xg and $Xg^1$ are independently selected from the group consisting of halogen, nitro, amino, carboxamido, lower alkyl, lower alkoxy, lower haloalkyl, lower alkylthio and the like; or Xg and $Xg^1$ can be taken together to form an —O(CH$_2$)$_n$O— bridge; wherein ng is 1 to about 3; and pg and qg are from 0 to 5, wherein the sum of pg and qg is less than or equal to 5.

6) Compounds Having General Formula VI

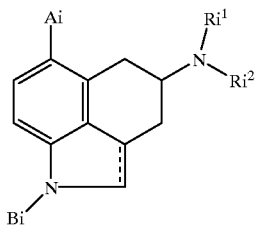
(VI)

wherein - - - - represents a single or a double bond;

$Ri^1$ is selected from the group consisting of hydrogen, lower alkyl, lower alkenyl, phenyl(lower)alkyl, cyclopropylmethyl, $CORi^4$, —(CH$_2$)$_{ni}$S(lower)alkyl, and —(CH$_2$)$_{ni}$C(O)NRi$^9$Ri$^{10}$;

$Ri^2$ is selected from the group consisting of hydrogen, lower alkyl, lower alkenyl, and cyclopropylmethyl;

Bi is selected from the group consisting of hydrogen, lower alkyl, and an amino-blocking group;

Ai is selected from the group consisting of a tetrazolyl ring, a substituted tetrazolyl ring, a 5-membered heterocyclic aromatic ring, a 6-membered heterocyclic aromatic ring, and the group

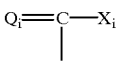

wherein said rings can have from one to three heteroatoms independently selected from the group consisting of sulfur, oxygen, and nitrogen; with the proviso that the 6-membered heterocyclic ring can only contain carbon and nitrogen and the further proviso that a 5-membered ring may contain no more than one oxygen or one sulfur but not both oxygen and sulfur;

Xi is selected from the group consisting of hydrogen —$ORi^3$, —$SRi^3$, and —$NRi^5Ri^6$;

$Ri^3$ is selected from the group consisting of lower alkyl, substituted lower alkyl, aryl, substituted aryl, aryl(lower)alkyl, substituted aryl(lower)alkyl, and cycloalkyl;

$Ri^4$ is selected from the group consisting of hydrogen, lower alkyl, lower haloalkyl, lower alkoxy, and phenyl;

$Ri^5$ and $Ri^6$ are independently selected from the group consisting of hydrogen, lower alkyl, phenyl(lower)alkyl, and phenyl, or $Ri^5$ and $Ri^6$ can be taken together to form a heterocyclic ring;

$Ri^9$ and $Ri^{10}$ are independently selected from the group consisting of hydrogen, lower alkyl, and cycloalkyl;

ni is 1 to 4; and Qi represents oxygen or sulfur.

7) The (R)-Enantiomer of Compounds Having General Formula VII

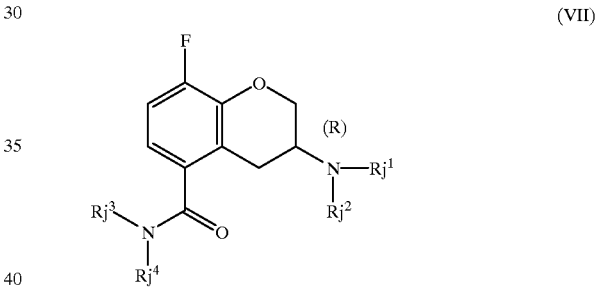
(VII)

wherein:

$Rj^1$ is n-propyl or cyclobutyl; $Rj^2$ is isopropyl, tertiary butyl, cyclobutyl, cyclopentyl or cyclohexyl; $Rj^3$ is hydrogen; and $Rj^4$ is hydrogen or methyl.

A preferred compound for practicing the subject invention is N-{2-[4-(2-methoxy-phenyl)-1-piperazinyl]ethyl}-N-(2-pyridinyl)cyclohexanecarboxamide, (COMPOUND A).

In another aspect, the present invention provides methods for treating neuromuscular dysfunction of the lower urinary tract in mammals that involve administering to affected mammals effective amounts for treating the dysfunction of a compound that:

(a) binds to a mammalian 5-HT$_{1A}$ receptor with an affinity of at least about $10^{-7}$M;

(b) binds to a mammalian 5-HT$_{1A}$ receptor with an affinity at least about 10-fold, and preferably about 50-fold stronger than the affinity with which the compound binds to a mammalian α1-adrenergic receptor; and (c) exhibits 5-HT$_{1A}$ receptor antagonist activity on both pre-synaptic and post-synaptic 5-HT$_{1A}$ receptors.

In yet another aspect, the invention provides methods for treating neuromuscular dysfunction of the lower urinary tract in mammals that involves administering to affected mammals an effective amount treating the dysfunction of a compound that exhibits 5-HT$_{1A}$ receptor antagonist activity on pre-synaptic and post-synaptic 5-HT$_{1A}$ receptors. Systems for ascertaining whether these criteria are met are described below.

Preferably, compounds to be used in practicing the present invention should have the requisite 5-HT$_{1A}$ receptor antagonist activity with an ID$_{50}$ of from about 1 to about 2000 µg/kg and a binding affinity to 5-HT$_{1A}$ receptors of at least about $10^{-7}$M. Compounds that bind 5-HT$_{1A}$ receptors less strongly (and thus require higher doses for therapeutic effect) will also be less selective under clinical conditions in binding 5-HT$_{1A}$ receptors relative to other receptors.

Administration of the 5-HT$_{1A}$ receptor antagonist compounds, their stereoisomers, pharmaceutically acceptable salts, hydrates or solvates may be achieved by any effective route, including oral, enteral, intravenous, intramuscular, subcutaneous, transmucosal, and by-inhalation routes, preferably by an oral or transdermal route.

Also provided are pharmaceutical formulations comprising the compounds described above in conjunction with pharmaceutically acceptable carriers and/or excipients.

In yet another aspect, the invention provides a method for identifying a compound useful for treating neuromuscular dysfunction of the lower urinary tract. The method is carried out using the steps of:

(a) individually measuring the binding affinity of test compounds for a 5-HT$_{1A}$ receptor and an α1-adrenergic receptor;

(b) identifying those test compounds that
  (1) bind to a 5-HT$_{1A}$ receptor with an affinity of at least about $10^{-7}$M; and
  (2) bind to a 5-HT$_{1A}$ receptor with an affinity at least about 10-fold stronger than the affinity with which the compound binds to a α1-adrenergic receptor;

(c) individually measuring the ability of each of the compounds identified in step (b) for 5-HT$_{1A}$ receptor antagonist activity on pre-synaptic 5-HT$_{1A}$ receptors and post-synaptic 5-HT$_{1A}$ receptors; and (d) selecting as useful compounds those compounds that exhibit 5-HT$_{1A}$ receptor antagonist activity on both pre-synaptic 5-HT$_{1A}$ receptors and post-synaptic 5-HT$_{1A}$ receptors. Preferably, compounds are selected that exhibit pre-synaptic and post-synaptic antagonist activities with an ID$_{50}$ of from about 1 to about 2000 µg/kg and a ratio of binding constants to 5-HT$_{1A}$ and α1-adrenergic receptors of 50.

Test compounds for screening in the above method may be selected from among a plurality of compounds having a protonatable nitrogen atom which is linked on one side, directly or indirectly, to an aromatic or heteroaromatic ring and to a carbon chain on the other side.

Preferably, the activity of compounds identified in step (d) above is confirmed by evaluating at least one of the following biological parameters: (1) inhibition of volume-induced rhythmic bladder voiding contractions in anesthetized rats; and (2) increase in bladder volume capacity in conscious rats. Useful compounds exhibit activity in at least one of these bioassays.

BRIEF DESCRIPTION OF THE DRAWINGS

FIG. 1 is a graphic illustration of a typical recorder tracing showing the effect of COMPOUND A on volume-induced bladder contractions of anaesthetized rats. The arrow indicates the intravenous administration of 300 µg/kg of COMPOUND A.

FIG. 2 is a graphic illustration of a typical recorder tracing showing the effect of COMPOUND A on cystometrographic parameters in conscious rats. The arrow indicates oral treatment of the animal with 3 mg/kg of COMPOUND A. BVC, bladder volume capacity; MP, micturition pressure.

DETAILED DESCRIPTION OF THE INVENTION

All patents, patent applications, and references cited herein are hereby incorporated by reference in their entirety. In the case of inconsistencies, the present description, including the present definitions, will control.

The present invention provides methods and compositions for treating neuromuscular dysfunction of the lower urinary tract, particularly those involving micturition (urination), such as dysuria, incontinence, and enuresis. The methods involve administering to affected individuals 5-HT$_{1A}$ receptor antagonists for a sufficient time and in an amount effective for lessening or ameliorating at least one symptom of the micturition disorder.

5-HT$_{1A}$ receptor antagonist compounds suitable for use in practicing the present invention include without limitation those compounds having one or more of the following properties:

(1) "True" 5-HT$_{1A}$ antagonist activity: Useful compounds preferably exhibit antagonist activity on both pre-synaptic (somatodendritic) and post-synaptic 5-HT$_{1A}$ receptors. Most preferably, the compounds exhibit full antagonist activity on both pre-synaptic and post-synaptic sites (i.e., are "true" antagonists and not "partial agonists" according to the definition of Fletcher et al., TiPS 14:441, 1993). As used herein, "pre-synaptic" 5-HT$_{1A}$ receptors include those present on 5-HT-producing neurons that are involved in autoregulation of 5-HT release; "post-synaptic" 5-HT$_{1A}$ receptors include those that are widely distributed throughout the mammalian brain and are coupled to potassium channels or adenylate cyclase.

(2) Selectivity: Preferred compounds exhibit at least about 10-fold less specific binding activity to α1-adrenergic receptors than to 5-HT$_{1A}$ receptors; most preferably, the compounds exhibit 50-fold less α1-binding activity than 5-HT$_1$A-binding activity.

Useful compounds preferably bind to 5-HT$_{1A}$ receptors with a K$_i$ of at least $10^{-7}$M, and most preferably with a K$_i$ of at least $10^{-8}$M.

Compounds of the invention which possess the requisite pre-synaptic and post-synaptic 5-HT$_{1A}$ antagonistic activity have a protonatable nitrogen atom which is linked on one side, directly or indirectly, to an aromatic or heteroaromatic ring and to a carbon chain on the other side. In addition, the protonatable nitrogen and the chain can form a ring. Accordingly, compounds belonging to this general class are suitable candidates for testing according to the methods taught below.

Compounds that bind 5-HT$_{1A}$ receptors and are therefore candidates for screening to identify compounds useful in treating neuromuscular dysfunction of the lower urinary tract are exemplified without limitation by N-{2-[4-(2-methoxyphenyl)-1-piperazinyl]ethyl}-N-(2-pyridinyl)cyclohexanecarboxamide, (COMPOUND A), and N-[2-[4-(4-Indolyl)-1-piperazinyl]ethyl]-N-(2-pyridyl)cyclohexanecarboxamide, (COMPOUND C).

Screening candidate compounds to identify those compounds that are useful in practicing the present invention involves: 1) Measuring the specific binding activity of the compound towards 5-HT$_{1A}$ and α-adrenergic receptors to identify those compounds that bind at least 10-fold more tightly to 5-$HT_{1A}$ receptors than to α-1-adrenergic receptors; and 2) Measuring the antagonist activity of the compound towards pre-synaptic and post-synaptic 5-$HT_{1A}$ receptors to identify compounds that exhibit antagonist activity towards both pre-synaptic and post-synaptic receptors.

Measurement of the specific binding activity of a compound towards different neuronal receptors (such as, e.g., 5-$HT_{1A}$ receptors according to the method of Alexander, B. S. et al., *J. Pharm. Pharmacol.* 40, 888–891, (1988); $α_1$-adrenergic receptors according to the method of Hanft, G. et al., *J. Pharm. Pharmacol.* 41, 714–716, (1989); $α_2$-adrenergic receptors according to the method of Cheung, Y-D. et al., *Eur J. Pharmacol.* 84, 79–85, (1982); dopamine $D_2$ receptors according to the method of Creese, I. et al., *Eur J. Pharmacol.* 60, 55–66, (1979); and 5-$HT_2$ receptors according to the method of Strekmeier, C. A. et al., *Life Sci.,* 38, 117–127, (1966)) may be achieved using any of a multiplicity of methods that are well-known in the art, such as, for example, competitive binding to native or cloned receptors. Typically, a biological source of, for example, a 5-$HT_{1A}$ receptor is used in which the receptor is present at a sufficiently high concentration so that binding of labelled 5-HT or a labelled 5-$HT_{1A}$ ligand is easily measurable. This source may comprise a mammalian tissue or fluid (either in situ or after removal from the animal) or a tissue culture cell. The target receptor may be expressed from either an endogenous (native) gene or from a transfected receptor-encoding recombinant gene. For example, the rat hippocampus is a rich (native) source of 5-$HT_{1A}$ receptors. Alternatively, human 5-$HT_{1A}$ receptor cDNA can be expressed in *E. coli* cells in culture as reported in Bertin B. et al., *J. Biol. Chem.* 267: 8200 (1992). Other cloned 5-HT receptors are described in Saxena, *Pharm.Ther.* 66:339, 1995. The ability of the test compound to compete with labelled 5-HT (or a labelled 5-$HT_{1A}$ ligand) for receptor binding is then measured, and a binding constant is calculated using Scatchard analysis or equivalent computational methods well-known in the art.

As discussed above, compounds useful in practicing the present invention bind to 5-$HT_{1A}$ receptors with a Ki of at least $10^{-7}$M, and bind to α1-adrenergic receptors with at least about 10-fold, preferably 50-fold, less affinity than they bind to 5-$HT_{1A}$ receptors. It will be understood that measurements of receptor binding affinity of a particular compound may vary depending upon the source of receptor, radiolabelled ligand, and other components, as well as specific assay conditions. To control for this type of variability, (N-{2-[4-(2-meth-oxyphenyl)-1-piperazinyl]ethyl}-N-(2-pyridinyl)cyclohexanecarboxamide) (COMPOUND A) and 1-(2-methoxyphenyl)-4-[4-(2-phthalimido)butyl]piperazine (COMPOUND Q, NAN-190) are included in all assays as standardization controls. That is, the values of binding constants obtained for compound A and compound Q are compared to the values reported below in Example 2, i.e., $K_i=3×10^{-10}$M for 5-$HT_{1A}$ receptors and $3×10^{-7}$M for α1-adrenergic receptor (COMPOUND A), and $K_i=1.9×10^{-9}$M for 5-$HT_{1A}$ receptors and $4.8×10^{-9}$M for α1-adrenergic receptors (COMPOUND Q). The values obtained in a particular assay for other test compounds are then normalized proportionately to the values obtained for Compound A and Compound Q in the same assay. For example, if in a particular experiment the $K_i$ of Compound A for 5-$HT_{1A}$ receptors is determined to be $3×10^{-9}$M, and for α1-adrenergic receptors is $3×10^{-8}$M, the values obtained for a test compound in the same assay for 5-$HT_{1A}$ receptors are divided by a factor of 10, and those obtained for α1-adrenergic receptors are multiplied by a factor of 10. This allows a direct comparison of absolute receptor binding activities and ratios of binding activities between different assays for the purpose of assessing whether the compound is within the scope of the invention.

Measurement of pre-synaptic and post-synaptic 5-$HT_{1A}$ receptor antagonist activity may be achieved using neurophysiological assay methods. For example, Raphe cell firing measured electrophysiologically is used as an index of pre-synaptic 5-$HT_{1A}$ receptor activity (Fletcher et al., *Eur. J. Pharmacol.* 237:283, (1993)). In this assay, a 5-$HT_{1A}$ receptor agonist acting at presynaptic somatodendritic 5-$HT_{1A}$ receptors inhibits Raphe neuronal firing, which is detected by measuring the electrical activity of 5-HT-containing neurons. Antagonists prevent the inhibitory action of the 5-$HT_{1A}$ receptor agonist, resulting in the maintenance of high levels of serotonin in the synaptic cleft. An alternative system for measuring pre-synaptic activity is the inhibition of 8-OH-DPAT-induced hypothermia in mice (Moser, *Eur. J. Pharmacol.* 193:165, 1991).

Inhibition of adenylate cyclase activity in rat hippocampal slices is used as an indicator of post-synaptic 5-$HT_{1A}$ receptor activity (Schoefter et al., *Brit. J. Pharmacol.* 95:975, (1988)). In this assay, compounds exhibiting antagonistic activity at post-synaptic 5-$HT_{1A}$ receptors antagonize the inhibitory effects of a 5-$HT_{1A}$ agonist on forskolin-stimulated adenylate cyclase activity and display no intrinsic effect on the basal activity of the enzyme. Alternative methods for measuring post-synaptic activity include inhibition of 8-OH-DPAT-induced behavioral syndrome, in particular the forepaw treading symptom (Tricklebank et al., *Eur. J. Pharmacol,* 117: 15, 1985). These and other methods are reviewed in Fletcher et al., TiPS 14:441, 1993.

Typically, a compound is tested for its ability to block the activity of 5-HT or 5-HT agonists in a dose-dependent manner. Antagonist activity is expressed as $ID_{50}$ in μg/kg. According to the present invention, a 5-$HT_{1A}$ receptor antagonist has a pre-synaptic antagonist activity of from about 1 to 2000 μg/kg and/or a post-synaptic antagonist activity of from about 1 to 2000 μg/kg. A compound is considered to be a "true" 5-$HT_{1A}$ receptor antagonist if it exhibits both pre-synaptic and post-synaptic antagonist activity. Preferred ranges for both pre-synaptic and post-synaptic antagonist activities are from about 1 to 200 μg/kg. As discussed above for binding assays, compound A is included in all assays as a positive control; the values obtained for the pre-synaptic and post-synaptic antagonistic activity of compound A are then compared with those disclosed below in Examples 6 and 7 ($ID_{50}$ for presynaptic= 8.5 μg/kg; post-synaptic=14 μg/kg), and the values obtained for other test compounds are normalized proportionately. For example, if in a particular experiment the $ID_{50}$ for Compound A is determined to be 0.85 μg/kg for pre-synaptic receptors and 140 μg/kg for post-synaptic receptors, the $ID_{50}$ values obtained for a test compound in the same experiment for pre-synaptic antagonism are multiplied by a factor of 10, and those obtained for post-synaptic are divided by a factor of 10, for the purpose of determining whether the compound is within the scope of the invention.

Once a compound is identified as possessing 5-$HT_{1A}$ receptor antagonist activity, its physiological activity can be confirmed using one or more animal model systems for neuromuscular dysfunction of the lower urinary tract. Useful animal model systems include, without limitation, volume-induced rhythmic bladder voiding contractions in anesthetized rats and cystometry in conscious rats. In one such method, the urinary bladder is catheterized, ligated, and connected with a pressure recording device. The bladder is then filled until reflex voiding contractions occur, after which the frequency and amplitude of the voiding contractions are measured. In another method, bladder volume capacity (BVC) and micturition pressure (MP) are measured one day following bladder catheterization. In the first method, the test compounds are administered intravenously prior to the measurements. Either an oral or intravenous administration route may be used in the second method. These methods are described in more detail in Examples 8 and 9 below, and were originally used to validate the predictive qualities of the "true" 5-HT$_{1A}$ receptor antagonist activity for the foregoing urinary tract disorders.

As measured using the first method, useful compounds exhibit an ED$_{50}$ for reducing the frequency of contractions of about 0.1–500 μg/kg, preferably 0.1–100 μg/kg; an ED$_{50}$ for reducing the amplitude of contractions of >1,000 μg/kg; and an ED$_{10}$ (extrapolated dose inducing 10-min disappearance of contractions) of about 0.1–2,000 μg/kg, preferably 0.1–400 μg/kg (see e.g., Table 3 and 4 below).

As measured using the second method, useful compounds, when administered intravenously, cause at least a 25% increase in BVC at a dose of about 10–20,000 μg/kg, preferably about 10–2,000 μg/kg, and reduce MP by less than 30% at doses >3,000 μg/kg, preferably >10,000 μg/kg (see, e.g., Tables 5 and 6 below.) When administered orally, useful compounds cause at least a 25% increase in BVC at a dose of about 20–50,000 μg/kg, preferably about 20–10,000 μg/kg, and reduce MP by less than 30% at doses >6,000 μg/kg, preferably >20,000 μg/kg.

Compounds of the invention which possess the requisite pre-synaptic and post-synaptic 5-HT$_{1A}$ antagonistic activity have at least one protonatable nitrogen atom which is linked on one side indirectly to an aromatic or heteroaromatic ring and to a carbon chain on the other side. In addition, the protonatable nitrogen and the chain can form a ring. Compounds belonging to this general class are suitable candidates for testing for applicability to treating neuromuscular dysfunction of the lower urinary tract according to the methods taught herein.

Examples of families of 5-HT$_{1A}$ receptor antagonist compounds for use in the present invention include without limitation:

1) Piperazine Derivatives Having General Formula I

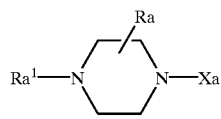

(I)

wherein:

Ra is selected from the group consisting of hydrogen, and lower alkyl;

Ra$^1$ is selected from the group consisting of aryl, nitrogen-containing heteroaryl, and bicyclic heteroaryl; and Xa is selected from the group consisting of

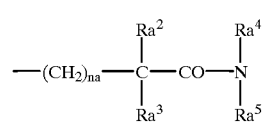

(Aa)

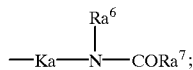

(Ba)

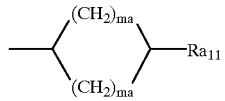

(Ca)

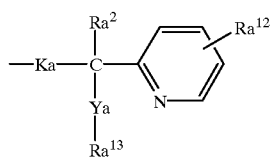

(Da)

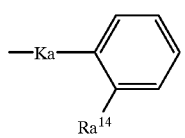

(Ea)

wherein na is 1 or 2; ma is 1, 2, or 3;

Ra$^2$ and Ra$^4$ are independently selected from the group consisting of hydrogen and lower alkyl;

Ra$^3$ is selected from the group consisting of aryl and aryl(lower)alkyl;

Ra$^5$ is selected from the group consisting of hydrogen, lower alkyl, cycloalkyl, and cycloalkyl(lower)alkyl; or Ra$^4$ and Ra$^5$ taken together with the nitrogen atom to which they are attached can form, a ring, such as, for example, an azetidino, pyrrolidino, piperidino, hexahydroazepino, morpholino, or piperazino ring; said ring can optionally be substituted by lower alkyl, aryl, or aryl(lower)alkyl.

Ka is a C$_2$–C$_4$ alkylene chain which can be optionally substituted by one or more lower alkyl groups;

Ra$^6$ is selected from the group consisting of a monocyclic heteroaryl radical and a bicyclic heteroaryl radical;

Ra$^7$ is selected from the group consisting of hydrogen, lower alkyl, cycloalkyl, cycloalkenyl, cycloalkyl(lower)alkyl, aryl, aryl(lower)alkyl, heteroaryl, heteroaryl(lower)alkyl, —NRa$^8$Ra$^9$, and —O—Ra$^{10}$;

wherein Ra$^8$ is selected from the group consisting of hydrogen, lower alkyl, aryl, and aryl(lower)alkyl;

Ra$^9$ is selected from the group consisting of hydrogen, lower alkyl, —CO—(lower)alkyl, aryl, —CO—aryl, aryl (lower)alkyl, cycloalkyl, and cycloalkyl(lower)alkyl; or Ra$^8$ and Ra$^9$ taken together with the nitrogen atom to which they are attached can form a saturated heterocyclic ring which optionally contains additional hetero atoms; and Ra$^{10}$ is selected from the group consisting of lower alkyl, cycloalkyl, cycloalkyl(lower)alkyl, aryl, aryl(lower)alkyl, heteroaryl, and heteroaryl(lower)alkyl;

Ra$^{11}$ is selected from the group consisting of aryl, and heteroaryl containing at least one nitrogen atom; and Ra$^{12}$ is hydrogen or lower alkyl;

Ra$^{13}$ is hydrogen, alkyl, cycloalkyl or cycloakyl(lower) alkyl; and

Ra$^{14}$ is aryl.

Ya is selected from the group consisting of carbonyl, alkylene, hydroxymethylene, hydroxyalkylene, hydroxycycloalkylene, and —S(O)$_{na}$; where na=0–2. In addition, the Ya groups can be unsaturated, having one or more multiple bonds, or saturated.

The preferred Ra¹ is an aryl radical, and particularly a phenyl radical containing a substituent in the ortho position or a 1-naphthyl radical optionally substituted in the 2 or 7 positions. Examples of a preferred Ra¹ groups are o-(lower) alkoxyphenyl, such as, for example, o-methoxyphenyl, or 1-naphthyl substituted with for example, (lower)alkoxy and the like.

When Ra⁶ is a bicyclic heteroaryl radical, both rings can contain hetero ring atom(s), or only one ring can contain hetero atom(s). In the latter instance, the radical Ra⁶ is connected to the compound of formula (I) via the ring containing the hetero atom(s).

Examples of the heteroaryl radical Ra⁶ include, but are not limited to, monocyclic radicals containing one hetero atom, such as, for example, pyridyl (particularly 2-pyridyl); monocyclic radicals containing two hetero atoms, such as, for example thiazolyl (particularly 2-thiazolyl); and bicyclic radicals containing one or two hetero atoms, such as, for example, quinolinyl or isoquinolinyl and particularly 2-quinolinyl.

When Ra¹¹ and Ra¹² are aryl, the preferred groups are phenyl. When Ra¹¹ is a heteroaryl radical, it is preferably pyridine, optionally substituted with one or more alkyl groups.

The methods of preparation of the piperazine derivatives having formula (I) are disclosed in the following references: GB 2,230,780 (EP 395,313), GB 2,230,781 (EP 395,312), GB 2,248,836 (EP 481,744), GB 2,255,337, GB 2,262,093, WO 94/15919, WO 94/15928, WO 94121610, WO 95/33743, and GB 2,277,517, hereby incorporated by reference in their entirety.

Preferred compounds having formula (I) include:

2,3,4,5,6,7-hexahydro-1-{4-[1-[4-(2-methoxyphenyl)-piperazin-yl]]-3-phenyl}butanoyl-1H-azepine, 2,3,4,5,6,7-hexahydro-1-{4-[4-(2-methoxyphenyl)-piperazin-1-yl]-2-phenyl}butanoyl-1H-azepine, N-{2-[4-(2-methoxyphenyl)-1-piperazinyl]ethyl}-N-(2-pyridinyl)-cyclohexanecarboxamide (compound A), 1-[2-(2-biphenyl)ethyl]-4-(2-methoxyphenyl)piperazine, N-[2-[4-(4-Indolyl)-1-piperazinyl]ethyl]-N-(2-pyridyl) cyclohexanecarboxamide (compound C), 1-[2-[(2-Pyridylamino)ethyl]4-(2-methoxyphenyl)piperazine], (compound B), and 1-[2-[(2-Pyridylamino)ethyl]-4-(4-indolyl)piperazine], (compound D), and their pharmaceutically acceptable acid addition salts.
2) Compounds Having General Formula II

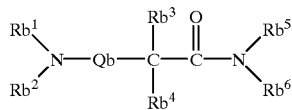

(II)

wherein

Qb represents a C₁₋₃alkylene chain, optionally substituted by one or more lower alkyl groups, Rb¹, Rb³, and Rb⁵, are independently selected from the group consisting of hydrogen, and lower alkyl; wherein Rb¹ and Rb² can be taken together to form a ring;

Rb⁴ is aryl, bicyclic aryl, or heteroaryl;

Rb⁶ is selected from the group consisting of hydrogen, C₁₋₁₀ alkyl, C₃₋₁₂ cycloalkyl, cycloalkyl(lower)alkyl, aryl or aryl(lower)alkyl;

wherein Rb⁵ and Rb⁶ can optionally be taken together with the nitrogen atom to which they are attached to form a saturated heterocyclic ring. Said ring can optionally contain an additional hetero atom to form, for example, an azetidino, pyrrolidino, piperidino, hexahydroazepino, morpholino, heptamethyleneimino, or piperazino ring; furthermore, said ring can optionally be substituted by, for example, lower alkyl, aryl, aryl(lower)alkyl, lower alkoxy, halogen or halo (lower)alkyl.

Rb² represents a group Ab, Bb, Cb, Db, Eb, or Fb, having the formulas:

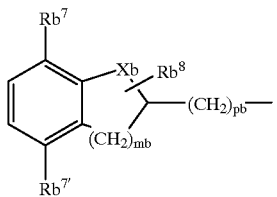

(Ab)

wherein Xb is selected from the group consisting of —(CH₂)ₙb—, —OCH₂—, and —SCH₂—, mb is 0 or 1, nb is 1, 2, or 3, and pb is 0 or 1; provided that the sum of mb and pb is 1; and that the sum of mb and nb is 1, 2, or 3;

Rb⁷ is selected from the group consisting of hydrogen, lower alkyl, lower alkoxy, hydroxy, halogen, trifluoromethyl, (lower)alkoxycarbonyl, carboxamido, nitro, cyano, amino, (lower)alkylamino, di(lower)alkylamino, and (lower)alkylcarbonyl;

Rb⁷' is selected from the group consisting of hydrogen and halogen; with the proviso that when Xb is —(CH₂)ₙb—, and Rb⁷' is hydrogen or halogen and when Xb is either —OCH₂—, or —SCH₂—, then —Rb⁷' is hydrogen.

Rb⁸ is hydrogen or lower alkyl; or

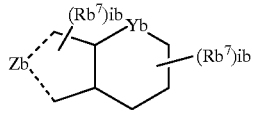

(Bb)

wherein Yb is selected from the group consisting of —O—, —S—, and —CH₂—;

Zb represents the atoms necessary to form a heteroaromatic ring, having from 5 to about 7 carbon atoms, fused to the non-aromatic ring containing the Yb group; and wherein each Rb⁷ group, attached to the heteroaromatic ring or the non-aromatic ring, independently represents one of the groups defined above; and each ib is independently 0, 1, or 2; or (Cb) Rb⁹—CH₂CH₂— wherein Rb⁹ represents a monocyclic or bicyclic heteroaryl group; or

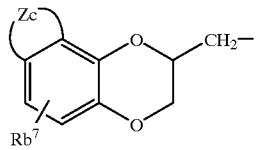

(Db)

where Rb⁷ is as defined above; and

Zc represents an optional fused aromatic or heteroaromatic ring, or if absent, hydrogen atoms; or (Eb) $Rb^{10}$—O—O—$CH_2CH(OH)CH_2$—; or (Fb) $Rb^{10}$—O—O—$CH_2CH_2$— where $Rb^{10}$ is selected from the group consisting of aryl, bicyclic aryl, and bicyclic heteroaryl.

The group

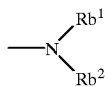

can represent the group

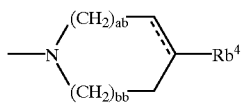

wherein ab and bb each independently represent 0, 1, 2, or 3 with the proviso that the sum of ab and bb is 0, 1, 2, or 3;

$Rb^4$ is as defined above; and

- - - - represents an optional double bond which can be present in the ring; provided that ab is at least 1.

An example of $Rb^4$ may be a bicyclic oxygen-containing radical of the formula:

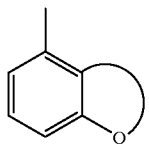

wherein the oxygen containing heterocyclic ring contains from about 5 to about 7 ring atoms, said heterocyclic ring being saturated or unsaturated and optionally includes one or more hetero ring atoms or groups, such as, for example, —O—, —S—, —$SO_2$— or —$NRb^3$— wherein $Rb^3$ represents a group deemed above, in addition to the oxygen atom illustrated.

The preparation of compounds having formula (II) are disclosed in International Patent applications WO 94/03444, and WO 94/20481.

A preferred compound having formula (II) is:
1-{4-[(1,4-benzodioxan)-2-ylmethylamino]-2-phenylbutanoyl}-2,3,4,5,6,7-hexahydro-1H-azepine.

3) Compounds Having General Formula III

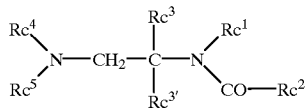

(III)

wherein $Rc^1$ represents a heteroaryl radical, or a bicyclic heteroaryl radical;

$Rc^2$ is cycloalkyl;

$Rc^3$, $Rc^{3'}$ and $Rc^4$ are each independently selected from the group consisting of hydrogen, and lower allyl; and $Rc^5$ is a group having the formula (Ab), (Bb), (Cb), (Db), (Eb), or (Fb) as defined above.

The group

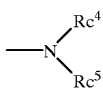

can represent the group

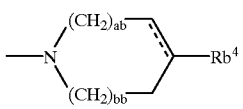

wherein ab, bb, and $Rb^4$ are as defined above, and represents a single or double bond; with the proviso that $Rb^4$ is not unsubstituted phenyl.

The compounds of formula (III) and their methods of preparation are disclosed in International Patent application WO 94/21611 and WO 95/02592.

Preferred compounds having formula (III) are:
N-[2-(1,4-benzodioxan-2-ylmethyl)methylamino]ethyl-N-(2-pyridinyl)-cyclohexanecarboxamide,
(R)-N-[2-[1-[4-(2-methoxyphenyl)piperidinyl]]propyl]-N-(2-pyridyl)cyclohexanecarboxamide,
(R)-N-[2-[1-[4-(2-thienyl)-1,2,3,6-tetrahydropyridyl]]propyl]-N-(2-pyridyl)cyclohexanecarboxamide.

4) Compounds Having General Formula IV

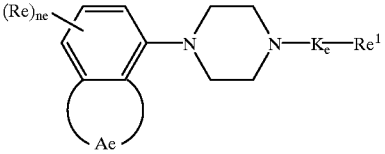

(IV)

wherein

Ae is selected from the group consisting of —OCH=CH—, —$OCH_2CH_2$—, —$O(CH_2)_{ne}O$—, —OCOCH=CH—; wherein ne is 1 or 2;

Each Re is independently selected from the group consisting of hydrogen, halogen, alkyl, hydroxy, alkoxy, trifluoromethyl, and cyano;

Ke is a linear or branched alkyl group having from 1 to 8 carbon atoms optionally substituted with an (hetero)aryl group;

$Re^1$ is selected from the group consisting of phenyl, thienyl, naphthyl, benzothiophenyl,

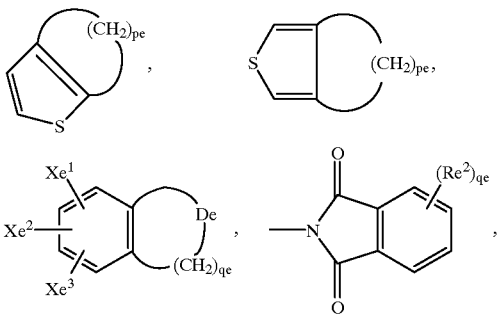

-continued

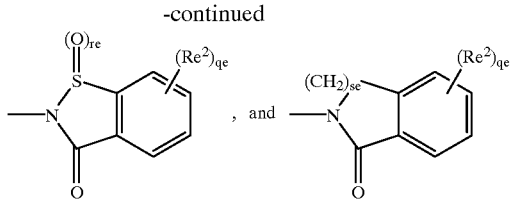

wherein pe is 3 or 4;
wherein each Re² is independently selected from the group consisting of halogen, alkyl, hydroxy, alkoxy, trifluoromethyl, and cyano; and
qe is 0 to 3; re is 0 to 2; and se is 1 or 2.

De is selected from the group consisting of —CH=CH—, and $(CH_2)_{2-4}$;

$Xe^1$, $Xe^2$, and $Xe^3$ are independently selected from the group consisting of hydrogen, alkyl, alkoxy, hydroxy, alkylthio, —$CF_3$, —$NO_2$, —$NH_2$, and —$NHCOCH_3$, or two of $Xe^1$, $Xe^2$, and $Xe^3$ can be taken together to form an —$OCH_2O$— or —$O(CH_2)_2O$— bridge.

The preparation of compounds having formula (IV) are disclosed in EP 490,772, EP 574,313, and EP 633,260.
Preferred compounds having formula IV include:
1-[5-(1,4-benzodioxanyl)]-4-[3-(3-thienyl)propyl]piperazine,
1-[5-(1,4-benzodioxanyl)]-4-[2-(1-indanyl)ethyl]piperazine, and
1-[5-(1,4-benzodioxanyl)]-4-[3-(1-benzocyclobutyl)propyl]piperazine.

5) Compounds Having General Formula V

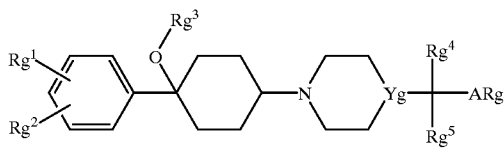

(V)

wherein $Rg^1$ and $Rg^2$ are independently selected from the group consisting of hydrogen, halogen, $CF_3$, and lower alkoxy; or when $Rg^1$ and $Rg^2$ are on adjacent carbon atoms, taken together, they can form an —$O(CH_2)_{ig}O$— bridge; wherein ig is from 1 to about 3; with the proviso that $Rg^1$ and $Rg^2$ cannot both be hydrogen.

$Rg^3$, $Rg^4$, and $Rg^5$ are independently selected from the group consisting of hydrogen, lower alkyl, and phenyl;
Yg is N or CH, and
ARg is selected from the group consisting of heteroaryl, substituted phenyl, and unsubstituted phenyl.
The ARg substituted phenyl groups have the formula Ag:

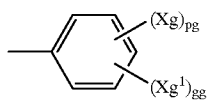

(Ag)

wherein Xg and $Xg^1$ are independently selected from the group consisting of halogen, nitro, amino, carboxamido, lower alkyl, lower alkoxy, lower haloalkyl, lower alkylthio and the like; or
Xg and $Xg^1$ can be taken together to form an —$O(CH_2)_{ng}O$— bridge; wherein ng is 1 to 3; and pg and qg are from 0 to 5, wherein the sum of pg and qg is less than or equal to 5.

The preparation of compounds having formula (V) is disclosed in U.S. Pat. No. 5,387,593 and EP 546,583.
Preferred compounds having formula V include:
Z and E-1-(1,4-benzodioxan-6-yl)4-[4-(phenylmethyl)-1-piperazinyl]-cyclohexanol, and
Z-1-[4-(1,3-benzodioxolan-5-yl)-4-methoxy-1-cyclohexyl]4-[(3-methoxy-phenyl)methyl]piperidine.

6) Compounds Having General Formula VI

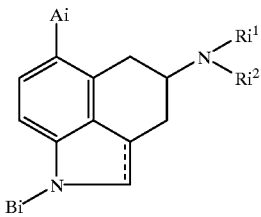

(VI)

wherein - - - - represents a single or a double bond;
$Ri^1$ is selected from the group consisting of hydrogen, lower alkyl, lower alkenyl, phenyl(lower)alkyl, cyclopropylmethyl, $CORi^4$, —$(CH_2)_{ni}S$(lower)alkyl, and —$(CH_2)_{ni}C(O)NRi^9Ri^{10}$;
$Ri^2$ is selected from the group consisting of hydrogen, lower alkyl, lower alkenyl, and cyclopropylmethyl;
Bi is selected from the group consisting of hydrogen, lower alkyl, and an amino-blocking group;

The term "amino-blocking group", as used herein, and as used in synthetic organic chemistry, refers to a group which will prevent an amino group from participating in a reaction carried out on another functional group in the molecule, but which can be removed from the amine when desired. Such groups are described by T. W. Greene in chapter 7 of "Protective Groups in Organic Synthesis, John Wiley and Sons, New York, 1981. Groups which are useful for the compounds of the invention include benzyl and substituted benzyl groups such as, for example, 3,4-dimethoxybenzyl, o-nitrobenzyl and triphenylmethyl, and the like; groups having the formula COOR wherein R includes groups such as, for example, methyl, ethyl, propyl, isopropyl, 2,2,2-trichloroethyl, 1-methyl-1-phenylethyl, isobutyl, t-amyl, vinyl, allyl, phenyl, benzyl, p-nitrobenzyl, o-nitrobenzyl, 2,4-dichlorobenzyl, and the like; acyl and substituted acyl groups such as, for example, formyl, acetyl, chloroacetyl, dichloroacetyl, trichloroacetyl, trifluoroacetyl, benzoyl, p-methoxybenzoyl, and the like; substituted sulfonyl groups such as, for example, methanesulfonyl, p-toluenesulfonyl, p-bromobenzenesulfonyl, p-nitrophenylethyl, p-toluenesulfonylaminocarbonyl, and the like. Preferred amino-blocking groups are benzyl, acyl [C(O)R] or $SiR_3$ where R is $C_{1-4}$ alkyl, halomethyl or 2-halo-substituted-($C_{2-4}$ alkoxy).

Ai is selected from the group consisting of a tetrazolyl ring, a substituted tetrazolyl ring, a 5-membered heterocyclic aromatic ring, a 6-membered heterocyclic aromatic ring, and the group

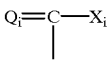

wherein said rings can have from one to three heteroatoms independently selected from the group consisting of sulfur, oxygen, and nitrogen; with the proviso that the 6-membered heterocyclic ring can only contain carbon and nitrogen and the further proviso that a 5-membered ring may contain no more than one oxygen or one sulfur but not both oxygen and sulfur;

Xi is selected from the group consisting of hydrogen —$ORi^3$, —$SRi^3$, and —$NRi^5Ri^6$;

$Ri^3$ is selected from the group consisting of lower alkyl, substituted lower alkyl, aryl, substituted aryl, aryl(lower)alkyl, substituted aryl(lower)alkyl, and cycloalkyl;

$Ri^4$ is selected from the group consisting of hydrogen, lower alkyl, lower haloalkyl, lower alkoxy, and phenyl;

$Ri^5$ and $Ri^6$ are independently selected from the group consisting of hydrogen, lower alkyl, phenyl(lower)alkyl, and phenyl, or $Ri^5$ and $Ri^6$ can be taken together to form a heterocyclic ring;

$Ri^9$ and $Ri^{10}$ are independently selected from the group consisting of hydrogen, lower alkyl, and cycloalkyl;

ni is 1 to 4; and Qi represents oxygen or sulfur.

The preparation of compounds having formula (VI) are disclosed in EP 444,854, EP 590,971 and U.S. Pat. No. 4,576,959.

Preferred compounds having Formula VI include:

(2aS,4R)-4-(di-n-propylamino)-6-aminocarbonyl-1,2,2$_a$,3,4,5-hexahydro-benz[c,d]indole, (2aS,4R)-N,N-dimethyl-4-(di-n-propylamino)-1,2,2$_a$,3,4,5-hexahydrobenz[c,d]-indole-6-carboxamide, (4R)-6-(5-isoxazolyl)-4-(di-n-propylamino)-1,3,4,5-tetrahydrobenz[c,d]indole, (4R)-6-(2-oxazolyl)4-(di-n-propylamino)-1,3,4,5-tetrahydrobenz[c,d]indole, (4R)-6-(5-oxazolyl)4-(di-n-propylamino)-1,3,4,5-tetrahydrobenz[c,d]indole, and (4R)-6-[2-(1,3,4-oxadiazolyl)]-4-(di-n-propylamino)-1,3,4,5-tetrahydro-benz[c,d]-indole.

7) The (R)-Enantiomer of Compounds Having General Formula VII

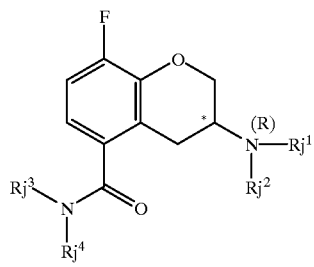

(VII)

wherein:

$Rj^1$ is n-propyl or cyclobutyl; $Rj^2$ is isopropyl, tertiary butyl, cyclobutyl, cyclopentyl or cyclohexyl; $Rj^3$ is hydrogen; and $Rj^4$ is hydrogen or methyl.

Preferred examples of compounds having formula VII are:

(R)-5-Carbamoyl-3-(N-tert-butyl-N-n-propylamino)-8-fluoro-3,4dihydro-2H-1-benzopyran;

(R)-5-Carbamoyl-3-(N,N-dicyclobutylamino)-8-fluoro-3,4-dihydro-2H-1-benzopyran;

(R)-5-Carbamoyl-3-(N-cyclobutyl-N-isopropylamino)-8-fluoro-3,4-dihydro-2H-1-benzopyran.

The synthesis of these compounds can be performed according to the following scheme:

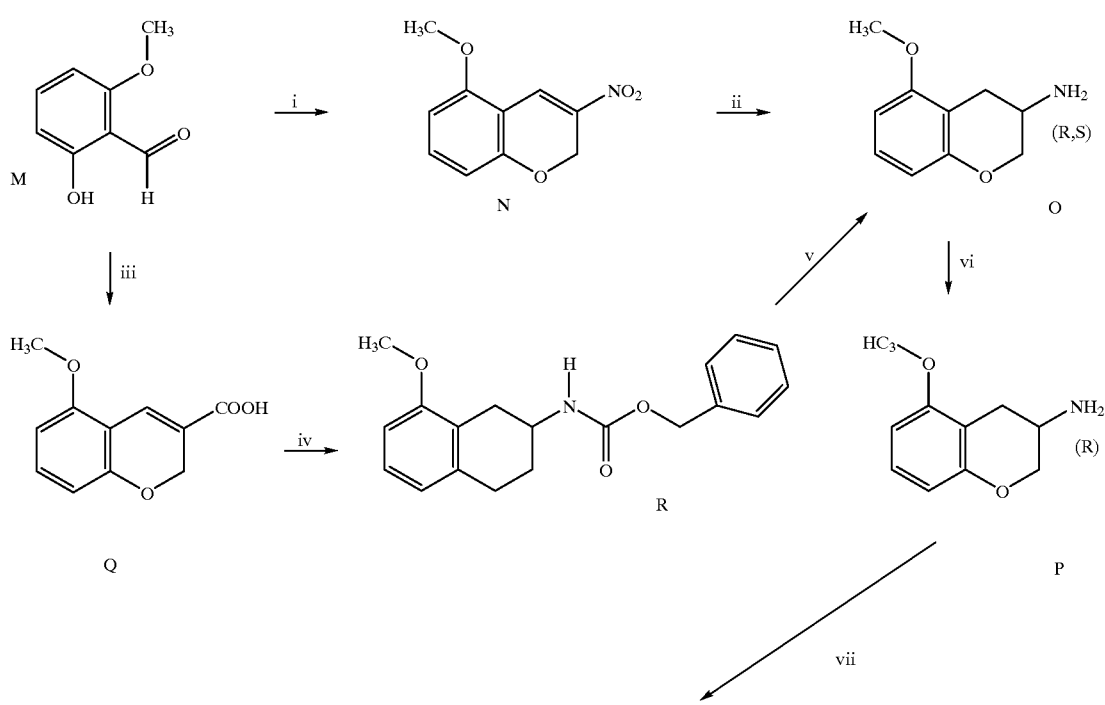

-continued

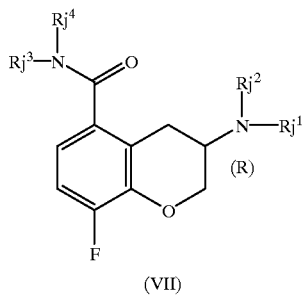

(VII)

The starting material, 2-hydroxy-6-methoxybenzaldehyde (M), is commercially available, e.g., from Aldrich Chemical Company, Milwaukee Wis., U.S.A., or alternatively can be prepared as described in S. O. Thorberg et al., Acta Pharm. Suec. 24, 169 (1987). Reaction of this aldehyde starting material with 2-nitroethanol in the presence of di-n-butylammonium chloride in I-pentyl acetate, at reflux, will provide the nitro-benzopyran (N), (Step I). This reaction is described in D. Dauzonne et al., Synthesis 1984, 348. The resulting nitro-benzopyran is converted to racemic aminochroman (O) by a two-step conversion of the nitro-benzopyran to the dihydroaminopyran (Step ii). This is described in M. Al Neirabeyeh et al., Eur. J. Med. Chem. 26, 497 (1991).

An alternative route to the dihydroaminopyran, O, again starting with Aldehyde M, is described in Thorberg et al., supra. Aldehyde M is reacted with acrylonitrile and 1,4-diazabicyclo[2.2.2]octane (DABCO) at reflux. The cyanobenzopyran is converted to the corresponding benzopyran carboxylic acid with aqueous sodium hydroxide. The benzopyran carboxylic acid (Q) is esterified using a mineral acid in ethanol and reduced by hydrogenation over 5% Pd/C to provide a chroman carboxylic acid. The chroman carboxylic acid is reacted with diphenylphosphorazidate and trimethylamine in benzene at reflux followed by addition of benzyl alcohol and an additional 24 hours at reflux. This provides a benzyloxycarbonyl (SOC) protected amine (R). Hydrogenation of the BOC protected amine provided racemic aminochroman (Q) (Step v). The racemic amine (Q) was resolved using the technique described in WO 93/07135 (Step vi). The resolved (R)-amine (P) is converted to a compound having formula VII following the procedures described in WO 95/11891 (Step vii).

As used herein, lower alkyl indicates radicals having from 1 to about 6 carbon atoms. Preferably these radicals contain from 1 to about 4 carbon atoms. Examples of "lower alkyl" radicals include such as, for example, methyl, ethyl, propyl, isopropyl, butyl, tert-butyl, pentyl, isopentyl, and the like.

The term lower alkenyl as used herein indicates radicals having from 2 to about 6 carbon atoms. Preferably these radicals contain from 2 to about 4 carbon atoms.

The cycloalkyl groups contain from 3 to about 12 carbon atoms and preferably from 5 to about 7 ring atoms. Non-limiting examples of cycloalkyl groups are cyclopentyl, cyclohexyl, cycloheptyl, and the like. A preferred cycloalkyl group is cyclohexyl. Cycloalkyl groups also include bicyclic, and tetracyclic groups, such as, for example, adamantyl, and the like.

As used herein, "aryl" refers to aromatic radicals having from 6 to about 12 carbon atoms, such as, for example, phenyl, naphthyl, and the like, which can optionally be substituted by one or more substituents. Preferred substituents include but are not limited to lower alkyl, such as those described above; lower alkoxy, such as, for example, methoxy, ethoxy, propoxy, butoxy, and the like; halogen; halo(lower)alkyl, such as, for example, trifluoromethyl, and the like; nitro; nitrile; amido; (lower)alkoxycarbonyl; amino; (lower)alkylamino; and di(lower)alkylamino. Two substituents on the aromatic ring can be taken together to form bicyclic ring system. A particularly preferred ring is benzodioxanyl.

The term halogen refers to fluorine, chlorine, and bromine. The preferred halogens are chlorine, and fluorine.

Examples of the preferred aryl(lower)alkyl groups include but are not limited to benzyl, or phenethyl, wherein the phenyl rings can be substituted by the substituents described above.

As used herein, heteroaryl refers to an aromatic radical containing one or more hetero atoms (e.g., oxygen, nitrogen, or sulphur) and which can be mono- or bicyclic. The monocyclic heteroaryl radical refers to an aromatic ring containing one or more nitrogen or other heteroatoms, such as, for example, pyridinyl, 2-thienyl, 2-furanyl, 1-methyl-2-pyrrolyl, pyrimidinyl, pyrazinyl, oxazolyl, thiazinyl and the like. Preferred heteroaryl radicals include 2-pyridinyl, 3-pyridinyl, 4-pyridinyl.

The heteroaryl groups can be optionally substituted by lower alkyl, such as those described above; lower alkoxy, such as, for example, methoxy, ethoxy, propoxy, butoxy and the like; halogen; halo(lower)alkyl, such as, for example, trifluoromethyl, and the like; nitro; nitrile; amido; (lower) alkoxycarbonyl; amino; (lower)alkylamino; and di(lower) alkylamino.

As used herein, bicyclic heteroaryl refers to phenyl rings fused with a second ring containing one or more heteroatoms. A particularly preferred heteroatom is nitrogen. Examples of the bicyclic heteroaryl radicals include, but are not limited to, indazolyl, quinolinyl, isoquinolinyl, indolyl, and the like. The bicyclic heteroaryl groups can be substituted by one or more substituents. A preferred bicyclic heteroaryl radical is indolyl substituted with alkoxycarbonyl groups.

Preferred Compounds

The following table illustrates preferred compounds according to the present invention, whose properties were tested in Examples 5–9 below.

| Structure | Compound | General Formula | Reference | Name |
|---|---|---|---|---|
| (structure) | A | I | GB 2255337 A (Ex. 3) | N-[2-[4-(2-Methoxyphenyl)-1-piperazinyl]ethyl]-N-(2-pyridinyl)cyclohexanecarboxamide |
| (structure) | B | I | GB 2255337 A (Ex. 2 intermediate for Compound A) | 1-[2-[(2-Pyridylamino)ethyl]-4-(2-methoxyphenyl)piperazine |
| (structure) | C | I | WO 95/33743 (Ex. 3d) | N-[2-[4-(4-Indolyl)-2-piperazinyl]ethyl]-N-(2-pyridyl)cyclohexanecarboxamide |
| (structure) | D | I | WO 95/33743 (Ex. 3c, intermediate for Compound C) | 1-[2-[(2-Pyridylamino)ethyl]-4-(4-indolyl)piperazine |

Therapeutic Applications

The present invention encompasses pharmaceutical formulations comprising the 5-$HT_{1A}$ receptor antagonist compounds listed above, as well as methods employing these formulations for treating neuromuscular dysfunction of the lower urinary tract such as dysuria, incontinence, and enuresis. Dysuria includes urinary frequency, nocturia and urgency. Incontinence syndromes include stress incontinence, urgency incontinence, and overflow incontinence. Enuresis refers to the involuntary passage of urine at night or during sleep. Without wishing to be bound by theory, it is believed that administration of 5-$HT_{1A}$ receptor antagonists prevents unwanted activity of the sacral reflex arc and/or cortical mechanisms that control micturition. Thus it is contemplated that a wide range of neuromuscular dysfunction of the lower urinary tract can be treated using the compounds of the present invention.

An "effective amount" of the compound for treating a urinary disorder is an amount that results in measurable amelioration of at least one symptom or parameter of the disorder. Urinary tract disorders and symptoms thereof include urgency, frequency, incontinence, urine leakage, enuresis, dysuria, hesitancy, and difficulty emptying bladder. An additional parameter is the volume of urine. An effective amount for treating the disorder can be determined by experimentation known in the art, such as by establishing a matrix of dosages and frequencies and comparing a group of experimental units or subjects to each point in the matrix. The exact amount to be administered to a patient may vary depending on the state and severity of the disorder and the physical condition of the patient. a measurable amelioration of any symptom or parameter may be determined by a physician skilled in the art or reported by the patient to the physician. It will be understood that any clinically or statistically significant attenuation of any symptom or parameter is within the scope of the invention. Clinically significant attenuation means perceptible to the patient and/or to the physician.

For example, a single patient may suffer from several symptoms of dysuria simultaneously, such as, for example, urgency and frequency, either or both of which may be reduced using the methods of the present invention. In the case of incontinence, any reduction in the frequency or volume of unwanted passage of urine is considered a beneficial effect of the present methods of treatment.

The compounds of the present invention may be formulated into liquid dosage forms with a physiologically acceptable carrier, such as, for example, phosphate buffered saline or deionized water. The pharmaceutical formulation may also contain excipients, including preservatives and stabilizers, that are well-known in the art. The compounds can be formed into solid oral or non-oral dosage units such as, for example, tablets, capsules, powders, and suppositories, and may additionally include excipients, including without limitation lubricant(s), plasticizer(s), colorant(s), absorption enhancer(s), bactericide(s), and the like. Modes of administration include oral and enteral, intravenous, intramuscular, subcutaneous, transdermal, transmucosal (including rectal and buccal), and by-inhalation routes. Preferably, an oral or transdermal route is used (i.e., via solid or liquid oral formulations, or skin patches, respectively).

The amount of the agent to be administered may range from about 0.01 to about 25 mg/kg/day, preferably from about 0.1 to about 10 mg/kg/day and most preferably from about 0.2–5 mg/kg/day. It will be understood that the pharmaceutical formulations of the present invention need not in themselves contain the entire amount of the agent that is effective in treating the disorder, as such effective amounts can be reached by administration of a plurality of doses of such pharmaceutical formulations.

In a preferred embodiment of the present invention, COMPOUND A is formulated in capsules or tablets each preferably containing 50–200 mg COMPOUND A, and is most preferably administered to a patient at a total daily dose of 50–400 mg, preferably 150–250 mg, and most preferably 200 mg for relief of urinary incontinence. In another preferred embodiment, COMPOUND C is formulated in tablets or capsules each preferably containing 20–100 mg, and is most preferably administered to a patient at a total daily dose of 20–150 mg, preferably 30–90 mg, and most preferably 60 mg, for relief of urinary incontinence.

The methods, tables and examples provided below are intended more fully describe preferred embodiments of the invention and to demonstrate its advantages and applicability without limiting its scope.

EXAMPLE 1

1-[2-[2-Pyridylamino]ethyl]-4-(2-methoxyphenyl) piperazine (Compound B)

23.5 g of 1-(2-aminoethyl)-4-(2-methoxyphenyl) piperazine [Hexachemie-Reuil Malmaison-France] and 4.85 mL of 2-chloropyridine were stirred at 160° C. in a closed reaction vessel for 10.5 hours. The reaction mixture was cooled to room temperature, dissolved in 320 mL of chloroform and washed with 1N sodium hydroxide (3×320 mL), followed by water (2×400 mL). The organic layer was dried (sodium sulfate) and evaporated to dryness under reduced pressure. The crude product was purified by column flash chromatography eluting with an ethyl acetate-3N $NH_3$ in methanol 100:2 mixture affording, after evaporation of the collected fractions, 5 g of the title compound as an oil. A sample was crystallized from ethyl acetate to give a solid melting at 89–94° C.

| | $^1$H-NMR ($CDCl_3$) | | |
|---|---|---|---|
| Chemical shifts (δ) | Multiplicity | protons | Assignments |
| 8.08 | ddd | 1 | CH at pos. 6 of pyridine |
| 7.40 | ddd | 1 | CH at pos. 4 of pyridine |
| 6.80–7.05 | m | 4 | 2-methoxyphenyl CHs |
| 6.55 | ddd | 1 | CH at pos. 5 of pyridine |
| 6.40 | dd | 1 | CH at pos. 3 of pyridine |
| 5.10 | bs | 1 | NH |
| 3.85 | s | 3 | $CH_3O$ |
| 3.38 | dt | 2 | $\underline{CH_2}NH$ |
| 3.00–3.15 | m | 4 | piperazine CHs |
| 2.60–2.75 | m | 6 | piperazine CHs and $CH_2N$ |

$D_2O$ addition makes NH signal appear upfield as HDO.

EXAMPLE 2

N-[2-[4-(2-Methoxyphenyl)-1-piperazinyl]ethyl]-N-(2-pyridyl)cyclohexane carboxamide.2.66 HCl.0.33 $H_2O$ (Compound A)

To a solution of 4.26 g of the compound of Example 1 in 42.5 mL of tetrahydrofuran, 6.52 mL of 2.5N n-butyllithium (hexane solution) was added dropwise at −22° C. After 40 minutes stirring at −20° C., 2.21 mL of cyclohexanecarbonyl chloride was added dropwise. The reaction mixture was stirred at −20° C. for 20 minutes, then at room temperature for 3.5 hours. Water was cautiously added to quench the reaction, followed by 3N sodium hydroxide. Ethyl acetate extraction followed by washing the organic layer with water, drying (sodium sulfate) and evaporating the solvent to dryness under reduced pressure gave an oily crude which was purified by column flash chromatography eluting with an ethyl acetate—3N $NH_3$ in methanol 100:2 mixture. Evaporation of the collected fractions afforded 5 g of the title compound as a base, which was converted into the hydrochloride by dissolution in methanol and addition of excess 2.8N HCl in diethyl ether. Evaporation to dryness of the solvents and desiccation of the solid in vacuo yielded 5.30 g of the title compound. M.p. 161–164° C.

Elemental analysis for C₂₅H₃₄N₄O₂ . 2.66 HCl . 0.33 H₂O

|  | C | H | N | Cl | H₂O |
|---|---|---|---|---|---|
| calc. % | 57.14 | 7.16 | 10.66 | 17.95 | 1.13 |
| found % | 57.45 | 7.29 | 10.67 | 18.13 | 1.20 |

¹H-NMR (D₆-DMSO)

| Chemical shifts (δ) | Multiplicity | protons | Assignments |
|---|---|---|---|
| 11.10–11.70 | bs | 1 | NH+ |
| 8.58 | dd | 1 | pyridine CH at pos. 6 |
| 8.05 | ddd | 1 | pyridine CH at pos. 4 |
| 7.64 | dd | 1 | pyridine CH at pos. 3 |
| 7.45 | dd | 1 | pyridine CH at pos. 5 |
| 6.82–7.10 | m | 4 | 2-methoxyphenyl CHs |
| 5.20–5.80 | bs | 2.4 | NH+ (remaining), H2O |
| 4.17 | t | 2 | CH2NCO |
| 3.79 | s | 3 | CH₃O |
| 3.00–3.75 | m | 10 | CH2N and piperazine CHs |
| 2.15–2.35 | m | 1 | cyclohexane CHCO |
| 0.85–1.85 | m | 10 | cyclohexane CHs |

D₂O addition makes NH signals appear upfield as HDO.

EXAMPLE 3

N-[2-[4-(4-Indolyl)-1-piperazinyl]ethyl]-N-(2-pyridyl)cyclohexanecarboxamide, HCl. 1.25 H₂O (COMPOUND C)

Step a: N-[(2,2-Dimethoxy)ethyl]-N-(2-pyridyl)cyclohexanecarboxamide

To a solution of 6 g of 2-[(2-pyridyl)amino]acetaldehyde dimethyl acetal (prepared as described in Beilstein E III/IV, 22, 3871) in 40 ml of tetrahydrofuran stirred at 0° C. was added dropwise 13.2 ml of butyl lithium (2.5 M solution in n-hexane) and the resulting mixture was stirred at room temperature for 1 h. Afterwards, to the solution was added dropwise in 5 min 4.46 ml of cyclohexanecarbonyl chloride. Stirring was continued for 5.5h, followed by in vacuo evaporation of the reaction mixture to dryness. The residue was purified by flash chromatography (chloroform-ethyl acetate 7:3) affording 13.3 g of the title compound.

¹H-NMR (CDCl₃)

| Chemical shifts (δ) | Multiplicity | protons | Assignments |
|---|---|---|---|
| 8.48–8.54 | m | 1 | pyridine H6 |
| 7.75 | ddd | 1 | pyridine H4 |
| 7.18–7.44 | m | 2 | pyridine H3,5 |
| 4.65 | t | 1 | CHCH₂ |
| 3.90 | d | 2 | CH₂ |
| 3.31 | s | 6 | CH₃O |
| 2.32 | tt | 1 | CH(CH₂)₂ |
| 0.8–1.85 | m | 10 | cyclohexane CH₂s |

Step b: N-Formylmethyl-N-(2-pyridyl)cyclohexanecarboxamide

A mixture of 1.46 g of N-[(2,2-dimethoxy)ethyl]-N-(2-pyridyl)cyclohexanecarboxamide, 0.05 g of 1,4-hydroquinone, and 25 ml of 2N HCl was stirred at 80° C. for 20 min under nitrogen stream. Afterwards, it was cooled at 0° C., diluted with 50 ml of methylene chloride, and alkalinized to pH=10 with 20% aqueous Na₂CO₃. The aqueous layer was extracted twice with methylene chloride and the combined organic layers were dried (sodium sulfate) and evaporated to dryness in vacuo affording 0.94 g of the title compound, used without further purification in the next reaction step.

¹H-NMR (CDCl₃)

| Chemical shifts (δ) | Multiplicity | protons | Assigmnents |
|---|---|---|---|
| 9.66 | s | 1 | CHO |
| 8.48–8.54 | m | 1 | pyridine H6 |
| 7.79 | ddd | 1 | pyridine H4 |
| 7.18–7.44 | m | 2 | pyridine H3,5 |
| 4.52 | s | 2 | CH₂ |
| 2.48 | tt | 1 | CH(CH₂)₂ |
| 0.8–1.95 | m | 10 | cyclohexane CH₂s |

Step c: N-[2-[4-(4-Indolyl)-1-piperazinyl]ethyl]-N-(2-pyridyl)cyclohexanecarboxamide HCL 1.25 H₂O A mixture of 0.94 g of N-formylmethyl-N-(2-pyridyl)cyclohexanecarboxamide, 0.69 g of 1-(4-indolyl)piperazine, 1.21 g of sodium triacetoxyborohydride, 0.44 ml of acetic acid and 30 ml of 1,2-dichloroethane was stirred at room temperature for 3 h. Afterwards, it was diluted with 20 ml of water and alkalinized to pH=10 with 20% Na₂CO₃. The aqueous layer was extracted twice with 1,2-dichloroethane and the combined organic layers were dried (sodium sulfate) and evaporated to dryness in vacuo affording a crude which was purified by flash chromatography (methylene chloride-methanol 98:2 to 95:5) affording 0.96 g of the title compound as a base. This was dissolved in 40 ml of methylene chloride and to the solution was added 3.8 N hydrogen chloride in diethyl ether. The precipitated title compound was filtered, yielding 0.66 g. M.p. 181–7° C.

EXAMPLE 4

1-(4-Indolyl)-4-[2-2-pyridylamino)ethyl]piperazine.3HCl.2H₂O (COMPOUND D)

Step a) 2-[4-(4-Indolyl)-1-piperazinyl]-N-(2-pyridyl)acetamide

A mixture of 1.4 g of 1-(4-indolyl)piperazine, 1.26 g of 2-chloro-N-(2-pyridyl)acetamide (prepared as described in Beilstein E III/IV, 22, 3881), 1.3 ml of diisopropylethylamine, and 14 ml of N,N-dimethylformamide was stirred at 60° C. under nitrogen stream for 4 h. Afterwards, the mixture was diluted with 200 ml of water and extracted with ethyl acetate (4×50 ml). The organic layers were washed with water, dried (sodium sulfate) and evaporated to dryness in vacuo affording 2.37 g of the title compound as a crude base, which was crystallized from MeOH affording 1.6 g melting at 198–201° C.

Step b: 1-(4-Indolyl)-4-[2-(2-pyridylamino)ethyl]piperazine.3HCl.2H₂O

To a solution of 1.04 g of 2-[4-(4-indolyl)-1-piperazinyl]-N-(2-pyridyl)acetamide in 30 ml of anhydrous tetrahydrofuran stirred at room temperature was added 0.34 g of 95% lithium aluminum hydride, and the resulting mixture was stirred at reflux for 10 h. Afterwards it was cooled, diluted with 7 ml 2N NaOH and 50 ml water, extracted with ethyl acetate (3×30 ml), washed with water, dried (sodium sulfate), and evaporated to dryness in vacuo affording 0.94 g of an oily residue. This was purified by flash chromatography (ethyl acetate-methanol 96:4 to 70:30) affording 0.76 g of the title compound as a base. This was dissolved in 20 ml of dichloromethane and to the solution was added an excess of 3.8 N hydrogen chloride in diethyl ether. The precipitated title compound was filtered and dried at 60° C. (0.5 mm Hg). M.p. (127)144–152° C.

EXAMPLE 5

Measurement of Binding of Test Compounds to $5HT_{1A}$ and $\alpha_1$ Adrenergic Receptors $^3[H]$ Prazosin Binding ($\alpha_1$ Receptors)

Rat cerebral cortices were homogenized in 50 volumes of ice-cold 50 mM Tris-HCl pH 7.4. The homogenates were centrifuged at 48,000×g for 10 minutes, and the pellets were resuspended in the same volume of ice-cold buffer, centrifuged, and resuspended two more times. The final pellets were resuspended in 100 volumes of 50 mM Tris-HCl, pH 7.4, containing 0.1% ascorbic acid and 10 $\mu$M pargyline. 1-mL samples were incubated for 30 min at 25° C. with 0.35 nM $^3[H]$prazosin, in the absence or presence of different concentrations ($10^{-5}$ to $10^{-10}$ M) of the test compound. Non-specific binding was determined in the presence of 10 $\mu$M phentolamine. The incubations were terminated by rapid filtration through Whatman GF/B filters using a Brandel cell harvester, after which the filters were washed with 3×3 mL of ice-cold buffer. The radioactivity retained on the filters was determined by liquid scintillation counting. The results are shown in the table below.

$^3[H]$8-OH-DPAT Binding ($5HT_{1A}$ receptors):

Rat hippocampi were homogenized in 50 volumes of ice-cold 50 mM Tris-HCl pH 7.4. The homogenates were centrifuged at 48,000×g for 10 minutes, and the pellets were resuspended in the same volume of ice-cold buffer, incubated for 10 minutes at 37° C., centrifuged and resuspended two more times. The final pellets obtained were resuspended in 100 volumes of 50 mM Tris-HCl, pH 7.4, containing 0.1% ascorbic acid and 10 $\mu$M pargyline. 1-mL samples were incubated for 30 min at 25° C. with 1 nM $^3[H]$8-OH-DPAT, in absence or presence of different concentrations ($10^{-5}$ to $10^{-10}$ M) of the test compound. Non-specific binding was determined in the presence of 10 $\mu$M 5-HT. The incubations were terminated by rapid filtration through Whatman GF/B filters using a Brandel cell harvester, after which the filters were washed with 3×3 mL of ice-cold buffer. The radioactivity retained on the filters was determined by liquid scintillation counting. The results are shown in the table below.

TABLE 1

Binding affinity for the $5-HT_{1A}$ receptor and $\alpha_1$-adrenergic receptor. Data are expressed as Ki(nM)

| Compound | $5-HT_{1A}$ | ($\alpha_1$-adrenergic receptor |
|---|---|---|
| A | 0.3 | 295.5 |
| B | 20.2 | 214.7 |
| C | 0.13 | 458.3 |
| D | 16.3 | 89.2 |
| Q | 1.9 | 4.8 |

These results indicate that Compounds A and C bind tightly and selectively to the $5-HT_{1A}$ receptor. By contrast, NAN-90 (compound Q) exhibits nearly equivalent binding to both receptors.

EXAMPLE 6

Measurement of Pre-Synaptic $5-HT_{1A}$ Receptor Antagonist Activity Antagonism of Hypothermia Induced by 8-OH-DPAT in Mice The antagonistic effect of $5-HT_{1A}$ receptor antagonists on hypothermia induced by 8-OH-DPAT was evaluated by the method of Moser (Moser, *Eur.J.Pharmacol.*, 193:165, 1991) with minor modifications as described below.

Male CD-1 mice (28–38 g) obtained from Charles River (Italy) were housed in a climate-controlled room (temperature 22±2° C.; humidity 55±15%) and maintained on a 12 h light/dark cycle with free access to food and water. On the day of experiment, mice were placed singly in clear plastic boxes under the same ambient conditions. Body temperature was measured by the insertion of a temperature probe (Termist TM-S, LSI) into the rectum to a depth of 2 cm. Rectal temperature was measured immediately prior to subcutaneous injection of the test compound and 30 min later. All animals then received 8-OH-DPAT (0.5 mg/kg s.c.) and their temperature was measured 30 min later. For each animal, temperature changes were calculated with respect to pretreatment values and the mean values were calculated for each treatment group.

A linear regression equation was used in order to evaluate $ID_{50}$ values, defined as the dose of antagonist needed to block 50% of the hypothermic effect induced by 0.5 mg/kg 8-OH-DPAT administered subcutaneously.

The results are shown in the following table.

TABLE 2

Antagonistic activity for the pre-synaptic $5-HT_{1A}$ receptor. Data are expressed as $ID_{50}$ (95% C.L.) in $\mu$g/kg s.c.

| Compound | $ID_{50}$ (95% C.L.) |
|---|---|
| A | 8.5 (5.8–12.5) |
| C | 1.9 (1.0–3.7) |
| Q | not active |

These results demonstrate that Compounds A and C have very potent pre-synaptic $5-HT_{1A}$ receptor antagonist activity.

EXAMPLE 7

Measurement of Post-Synaptic $5-HT_{1A}$ Receptor Antagonist Activity Inhibition of Forepaw Treading Induced by 8-OH-DPAT in Rats The inhibitory effect of $5-HT_{1A}$ receptor antagonists on the forepaw treading induced in rats by subcutaneous injection of 8-OH-DPAT was evaluated by the method of Tricklebank (Tricklebank et al., *Eur. J. Pharmacol.*, 117:15, 1985) with minor modifications as described below.

Male Sprague-Dawley rats (150–175 g) obtained from Charles River (Italy), were housed in a climate-controlled room and maintained on a 12 h light/dark cycle with free access to food and water. On the day of experiment, rats were placed singly in clear plastic boxes. Reserpinised rats were treated with reserpine, 1 mg/kg s.c., 18–24 h before the test to deplete intracellular stores of noradrenaline. For evaluation of antagonistic activity, compounds were i.p. or s.c. administered 16 min before 8-OH-DPAT (1 mg/kg s.c.). Observation sessions of 30 s duration began 3 min after treatment with the agonist and were repeated every 3 min over a period of 15 min.

The appearance of the forepaw treading symptom induced by postsynaptic stimulation of the $5HT_{1A}$ receptors was noted, and its intensity was scored using a ranked intensity scale in which: 0=absent, 1=equivocal, 2=present and 3=intense. Behavioral scores for each treated rat were accumulated over the time course (5 observation periods) and expressed as mean values of 8–10 rats.

A linear regression equation was used in order to evaluate $ID_{50}$ values, defined as the dose of antagonist needed to block 50% of the forepaw treading intensity induced by 1 mg/kg 8-OH-DPAT administered subcutaneously.

The results are shown in the following table.

| COMPOUND | NORMAL RATS $ID_{50}$ (µg/kg) | RESERPINIZED RATS $ID_{50}$ (µg/kg) |
| --- | --- | --- |
| COMPOUND A (s.c.) | 14 (12–16) | 8.5 (5.8–12.5) |
| COMPOUND Q (i.p.) | 700 (500–1000) | 2000 (1600–2400)* |

*inactive

These results demonstrate that Compound A exhibits significant post-synaptic $5\text{-}HT_{1A}$ receptor antagonist activity. Compound Q, by contrast, is much less active. Taken together, the bioassays for pre-synaptic and post-synaptic antagonist activity are effective for identifying compounds that exhibit both activities at levels that render them useful in treating urinary tract disorders.

EXAMPLE 8

Effect of $5\text{-}HT_{1A}$ Receptor Antagonists on Volume-Induced Rhythmic Bladder Voiding Contractions in the Anaesthetized Rats a. Methods:

Female Sprague Dawley rats weighing 225–275 g (Crl: $CD^0$ BR, Charles River Italia) were used. The animals were housed with free access to food and water and were maintained on a forced 12 h alternating light-dark cycle at 22–24° C. for at least one week, except during the experiment. The activity on the rhythmic bladder voiding contractions was evaluated according to the method of Dray (*J. Pharmacol. Methods*, 13:157, 1985), with some modifications as in Guarneri (*Pharmacol. Res.*, 27:173, 1993). Briefly, rats were anesthetized by subcutaneous injection of 1.25 g/kg (5 ml/kg) urethane, after which the urinay bladder was catheterized via the urethra using PE 50 polyethylene tubing filed with physiological saline. The catheter was tied in place with a ligature around the external urethral orifice and was connected with conventional pressure transducers (Statham P23 ID/P23 XL). The intravesical pressure was displayed continuously on a chart recorder (Battaglia Rangoni KV 135 with DCl/TI amplifier). The bladder was then filled via the recording catheter by incremental volumes of warm (37° C.) saline until reflex bladder voiding contractions occurred (usually 0.8–1.5 ml). Two parameters were recorded from the cystometrogram: the frequency of voiding contractions, calculated by counting the number of peaks/15 min of observation, and the mean amplitude of these contractions (mean height of the peaks in mmHg) in the same time period. For intravenous (i.v.) injection of bioactive compounds, a PE 50 polyethylene tubing filled with physiological saline was inserted into the jugular vein.

Bioactivity was assessed in individual animals (using 6–10 rats per dose), by recording the number and height of the peaks for 15 min after drug injection and comparing them with those previously recorded for 15 min after the intravenous administration of vehicle alone. In the evaluation of the mean amplitude of peaks after treatment, only the results from the cystometrograms showing a reduction in the frequency of contractions of $\leq 50\%$ were utilized. The statistical significance of changes in frequency and amplitude before and after treatment was assessed by the Student's t test for paired data. Changes showing a probability $P<0.01$ were considered significant.

An all-or-none criterion was also used to compare bioactivity in terms of $ED_{50}$ values. Rats showing a treatment-related change of $\geq 30\%$ relative to the basal value were considered to be positive. Quantal dose-response curves and $ED_{50}$ values were evaluated by the method of Bliss (*J. Pharm. Pharmacol.*, 11:192, 1938). In addition, since most compounds produced an effect that was relatively rapid in onset and led to a complete cessation of bladder contractions (as shown in FIG. 1), bioactivity was conveniently estimated by measuring the duration of bladder quiescence (i.e., the duration of time during which no contractions occurred). To compare the potency of the tested compounds in inhibiting the frequency of the bladder voiding contractions, equieffective doses producing 10 minutes of disappearance time ($ED_{10\ min}$) were computed by means of least square linear regression analysis.

B. Results

The rapid distension of the urinary bladder in urethane-anesthetized rats produced a series of rhythmic bladder voiding contractions whose characteristics have been described (Maggi et al., *Brain Res.*, 380:38, 1986; Maggi, et al., *J. Pharmacol. Exp. Ther.*, 230:500, 1984). The frequency of these contractions is related to the sensory afferent arm of reflex micturition and to the integrity of the micturition center, while their amplitude is a property of the efferent arm of the reflex (Maggi et al., *J. Pharmacol. Meth.*, 15:157, 1986; Maggi et al., *Brain Res.*, 415:1, 1987; Maggi et al., *Naun. Schmied. Arch. Pharmacol.*, 332:276, 1986; Maggi et al., *J. Urol.*, 136:696, 1986). In this model system, compounds that act mainly on the CNS (such as morphine) cause a reduction in voiding frequency, whereas drugs that act at the level of the detrusor muscle lower the amplitude of the bladder contractions.

A typical tracing is shown in FIG. 1, where the effects of 300 μg 11 cg i.v. COMPOUND A are shown. In the basal period (15 min before the arrow) 9 peaks were recorded. After the i.v. administration of 300 μg/kg of COMPOUND A (at the arrow), 14.2 min of bladder quiescence was observed (disappearance time; no contractions). No changes in the height of the peaks were observed.

The results are tabulated in Tables 3 and 4 below.

TABLE 3

Effects on rhythmic bladder voiding contractions after intravenous administration. Data represent the mean values ± S.E. of the number of contractions observed before and after the i.v. administration of the tested compounds, as well as the amplitude of the peaks recorded in animals showing a reduction of the frequency ≦ 50%. The $ED_{50}$ (and 95% confidence limits) values were evaluated on the basis of quantal criterion as descibed in the Methods.

| COMPOUND Dose (μg/kg i.v.) | No. of rats | FREQUENCY No. contr./15 min before | after treat. | AMPLITUDE mm Hg before | after treat. |
|---|---|---|---|---|---|
| COMPOUND A | | | | | |
| 1 | 10 | 11.7 ± 1.0 | 11.6 ± 1.3 | 25.4 ± 2.0 | 23.1 ± 1.9* |
| 3 | 10 | 11.5 ± 0.7 | 9.1 ± 1.0* | 25.1 ± 2.2 | 21.7 ± 2.0* |
| 10 | 10 | 11.5 ± 1.5 | 5.9 ± 1.6* | 26.0 ± 3.8 | 21.1 ± 1.0 |
| 30 | 10 | 11.8 ± 0.7 | 3.8 ± 0.7* | 28.5 ± 2.5 | 25.0 ± 4.0 |
| 100 | 10 | 12.0 ± 0.9 | 4.1 ± 1.1 | 28.0 ± 4.6 | 25.7 ± 2.9 |
| 300 | 10 | 9.5 ± 0.6 | 2.2 ± 0.5* | n.c. | n.c. |
| $ED_{50}$ (μg/kg) | | 5 (3 ÷ 8) | | | n.a. |
| FLAVOXATE | | | | | |
| 300 | 5 | 9.2 ± 1.2 | 8.8 ± 1.7 | 25.9 ± 1.3 | 24.1 ± 1.8 |
| 1000 | 17 | 10.1 ± 0.7 | 8.6 ± 0.9 | 26.1 ± 2.3 | 25.0 ± 2.2 |
| 3000 | 21 | 10.7 ± 0.7 | 6.5 ± 0.7* | 18.9 ± 0.9 | 16.6 ± 1.2 |
| 10000 | 20 | 11.3 ± 0.8 | 5.5 ± 0.6* | 19.9 ± 1.6 | 19.2 ± 1.5 |
| $ED_{50}$ (μg/kg) | | 2650 (1430 ÷ 4910) | | | n.a. |
| OXYBUTYNIN | | | | | |
| 30 | 6 | 14.8 ± 1.9 | 15.5 ± 2.3 | 26.7 ± 2.7 | 23.3 ± 2.5 |
| 100 | 6 | 13.3 ± 1.1 | 14.7 ± 1.0 | 25.0 ± 3.7 | 18.7 ± 2.7* |
| 300 | 12 | 10.1 ± 0.7 | 8.8 ± 0.8 | 20.9 ± 1.7 | 13.6 ± 0.8* |
| 1000 | 13 | 9.7 ± 0.8 | 9.5 ± 0.8 | 20.3 ± 2.4 | 11.8 ± 1.2* |
| 3000 | 13 | 10.0 ± 0.7 | 9.9 ± 1.5 | 18.0 ± 1.4 | 10.8 ± 1.0* |
| $ED_{50}$(μg/kg) | | n.a. | | | 240 (140 ÷ 400) |
| COMPOUND Q[A] | | | | | |
| 30 | 10 | 13.5 ± 1.2 | 11.8 ± 1.5 | 30.2 ± 3.7 | 26.1 ± 3.1* |
| 100 | 10 | 13.6 ± 1.0 | 6.4 ± 1.1* | 22.5 ± 1.7 | 17.3 ± 2.9 |
| 300 | 11 | 11.8 ± 1.1 | 6.6 ± 1.1* | 24.1 ± 1.8 | 17.6 ± 1.7* |
| $ED_{50}$(μg/kg) | | 46 (23 ÷ 92) | | | n.a. |
| COMPOUND B | | | | | |
| 30 | 6 | 9.7 ± 1.0 | 7.2 ± 1.3 | 29.6 ± 7.4 | 24.0 ± 6.2 |
| 100 | 6 | 9.7 ± 1.0 | 4.5 ± 1.6* | 19.0 ± 0.0 | 15.5 ± 0.1* |
| 300 | 6 | 12.7 ± 1.5 | 2.2 ± 0.9* | n.c. | n.c. |
| 1000 | 6 | 11.2 ± 1.0 | 4.0 ± 1.4 | 40.0 ± 0.0 | 25.5 ± 0.5 |
| $ED_{50}$(μg/kg) | | 54 (33 ÷ 91) | | n.c. | n.c. |
| COMPOUND C | | | | | |
| 0.3 | 6 | 10.7 ± 1.4 | 11.3 ± 1.7 | 31.0 ± 3.7 | 27.7 ± 4.1 |
| 1 | 6 | 11.7 ± 1.5 | 8.7 ± 1.3 | 26.5 ± 4.3 | 22.7 ± 5.1* |
| 3 | 6 | 9.7 ± 0.8 | 4.7 ± 1.1* | 33.7 ± 4.3 | 25.3 ± 1.2 |
| 10 | 6 | 11.7 ± 1.7 | 4.2 10.9* | 19.0 | 17.0 |
| 30 | 6 | 12.0 ± 1.1 | 4.5 ± 1.4 | n.c. | n.c. |
| $ED_{50}$(μg/kg) | | 1(0.6 ÷ 2) | | | n.a. |
| COMPOUND D | | | | | |
| 30 | 6 | 9.3 ± 0.8 | 9.5 ± 1.3 | 27.0 ± 2.4 | 23.8 ± 2.6* |
| 100 | 6 | 15.3 ± 1.0 | 9.3 ± 2.8 | 27.0 ± 1.5 | 23.7 ± 1.5* |

TABLE 3-continued

Effects on rhythmic bladder voiding contractions after intravenous administration. Data represent the mean values ± S.E. of the number of contractions observed before and after the i.v. administration of the tested compounds, as well as the amplitude of the peaks recorded in animals showing a reduction of the frequency ≦ 50%. The $ED_{50}$ (and 95% confidence limits) values were evaluated on the basis of quantal criterion as descibed in the Methods.

| COMPOUND Dose (μg/kg i.v.) | No. of rats | FREQUENCY No. contr./15 min before | after treat. | AMPLITUDE mm Hg before | after treat. |
|---|---|---|---|---|---|
| 300 | 6 | 13.2 ± 2.7 | 4.2 ± 2.2* | 26.0 | 20.0 |
| 1000 | 6 | 10.2 ± 0.6 | 4.2 ± 1.5* | 32.0 ± 5.0 | 23.5 ± 5.5 |
| $ED_{50}$ (μg/kg) | | 77(49 ÷ 122) | | | n.a. |

*= p ≦ 0.01 (Student's *t* test for paired data)
n.c. = not calculated
n.a. = not active on the parameter
A) = higher doses were not tested because of the high toxicity and low solubility of this compound.

TABLE 4

Effects on rhythmic bladder voiding contractions after intravenous administration. Data represent the mean values ± S. E. of the duration of bladder quiescence (disappearance time of contractions in min). The $ED_{10\ min}$ values represent the extrapolated dose inducing 10 min of disappearance of the contractions.

| COMPOUND Dose (μg/kg i.v.) | No. of rats | BLADDER CONTRACTIONS Disappearance time (min) |
|---|---|---|
| COMPOUND A | | |
| 1 | 10 | 1.34 ± 0.23 |
| 3 | 10 | 2.15 ± 0.42 |
| 10 | 10 | 8.13 ± 1.90 |
| 30 | 10 | 8.87 ± 3.16 |
| 100 | 10 | 12.56 ± 2.07 |
| 300 | 10 | 13.37 ± 1.83 |
| $ED_{10\ min}$ (μg/kg) | | 37 (18 ÷ 77) |
| COMPOUND B | | |
| 30 | 6 | 4.00 ± 1.87 |
| 100 | 6 | 9.60 ± 2.37 |
| 300 | 6 | 12.37 ± 2.63 |
| 1000 | 6 | 14.00 ± 4.45 |
| $ED_{10\ min}$ (μg/kg) | | 173 (28 ÷ 1087) |
| COMPOUND C | | |
| 0.3 | 6 | 1.10 ± 0.16 |
| 1 | 6 | 4.33 ± 1.30 |
| 3 | 6 | 7.58 ± 2.15 |
| 10 | 6 | 10.00 ± 0.92 |
| 30 | 6 | 8.85 ± 1.53 |
| $ED_{10\ min}$ (μg/kg) | | 9 (3 ÷ 24) |
| COMPOUND D | | |
| 30 | 6 | 1.63 ± 0.50 |
| 100 | 6 | 6.55 ± 2.24 |
| 300 | 6 | 12.75 ± 2.45 |
| 1000 | 6 | 9.37 ± 2.44 |
| $ED_{10\ min}$ (μg/kg) | | 181 (89 ÷ 366) |
| FLAVOXATE | | |
| 300 | 5 | 1.70 ± 0.60 |
| 1000 | 17 | 3.04 ± 0.96 |

TABLE 4-continued

Effects on rhythmic bladder voiding contractions after intravenous administration. Data represent the mean values ± S. E. of the duration of bladder quiescence (disappearance time of contractions in min). The $ED_{10\ min}$ values represent the extrapolated dose inducing 10 min of disappearance of the contractions.

| COMPOUND Dose (μg/kg i.v.) | No. of rats | BLADDER CONTRACTIONS Disappearance time (min) |
|---|---|---|
| 3000 | 21 | 5.30 ± 1.00 |
| 10000 | 20 | 8.25 ± 1.90 |
| $ED_{10\ min}$ (μg/kg) | | >10000 |
| COMPOUND Q[(A)] | | |
| 30 | 10 | 1.80 ± 0.52 |
| 100 | 10 | 6.34 ± 1.18 |
| 300 | 11 | 5.47 ± 1.93 |
| $ED_{10\ min}$ (μg/kg) | | >>300 |

[(A)]= higher doses were not tested because of the high toxicity and low solubility of this compound.

COMPOUNDS A–D, after intravenous administration, dose-dependently inhibited the frequency of the rhythmic bladder voidings with no effect on their amplitude. Of the test compounds shown, COMPOUNDS A and C were the most potent.

By contrast, oxybutynin was only effective at reducing the amplitude of the contractions, confirming that its effects are due to a complete inhibition of the muscarinic receptors in the bladder.

The compounds that reduced the contraction frequency induced a complete and transient disappearance of contractions for a time period that was directly proportional to the administered dose (Table 4).

Tables 3 and 4 also illustrate the effects on volume-induced bladder contractions of flavoxate, a drug widely utilized in clinical therapy for bladder dysfunctions. Administration of this drug resulted in suppression of bladder contractions. The mean disappearance time observed after administration of the highest tested dose (10,000 μg/kg i.v.) was 8.25±1.90 min. COMPOUND Q at the highest tested doses of 100–300 μg/kg gave a maximum disappearance time ranging from 5.5 to 6.3 min. (higher doses were not tested because of the high toxicity and low solubility of this compound).

These results indicate that COMPOUND C is the most potent compound in reducing the frequency of the voiding contractions when compared to flavoxate and COMPOUND Q in terms of both absolute potency ($ED_{50}$) and disappearance time ($ED_{10\ min}$). Its mechanism of action appears to be different from that of oxybutynin, a peripheral antimuscarinic. Furthermore, its effects appeared at very low doses.

EXAMPLE 9

Effect of 5-$HT_{1A}$ Receptor Antagonists on Cystometric Parameters in the Conscious Rat A. Methods:

Male Sprague Dawley rats (Crl: $CD^0$ BR) weighing 250–350 g were used. The animals were housed with free access to food and water and maintained on a forced 12 h alternating light-dark cycle at 22–24° C. for at least one week, except during performance of the experiment.

To quantify urodynamic parameters in conscious rats, cystometrographic studies were performed using procedures described in Pietra et al., *IRCS Med. Sci.*, 14:992, 1986; and Guarneri et al., *Pharmacol. Res.*, 24:175, 1991.

Male rats were anesthetized with nembutal (30 mg/kg) and chloral hydrate (125 mg/kg) i.p. and were placed in a supine position. An approximately 10 mm long midline incision was made in the shaved and cleaned abdominal wall. The urinary bladder was gently freed from adhering tissues, emptied, and then cannulated, via an incision at the dome, with a polyethylene cannula (Portex PP30), which was permanently sutured with silk thread. The cannula was exteriorized through a subcutaneous tunnel in the retroscapular area, where it was connected with a plastic adapter to avoid the risk of removal by the animal. For intravenous (i.v.) injection of test compounds, a PE 50 polyethylene tubing filled with physiological saline was inserted into the jugular vein and exteriorized in the retroscapular area.

Since cystometrographic parameters have been reported to be influenced by the time elapsed after catheter implantation Yaksh et al. *Amer. J. Physiol.*, 251:R1177, 1986, the rats were utilized exclusively one day after implantation.

On the day of the experiment, the rats were placed in Bollman's cages; after a stabilization period of 20 min, the free tip of the bladder catheter was connected through a T-shaped tube to a pressure transducer (Bentley T 800/Marb P 82) and to a peristaltic pump (Gilson minipuls 2) for a continuous infusion, at the constant rate of 0.1 ml/min, of saline solution into the urinary bladder. The intraluminal pressure signal during infusion was continuously recorded on a polygraph (Battaglia Rangoni KO 380 with ADCl/T amplifier). Two urodynamic parameters were evaluated: bladder volume capacity (BVC) and micturition pressure (MP). BVC (in ml) is defined as the minimum volume infused after which detrusor contraction (followed by micturition) occurs. MP (in mmHg) is defined as the maximal intravesical pressure induced by the contraction of detrusor during micturition. Basal BVC and MP values were calculated as the means of the first two recorded cystometrograms. At this point, the infusion was interrupted and the test compounds were administered. Fifteen minutes after intravenous administration, or one hour after oral drug administration, two additional cystometrograms were recorded in each animal and the mean values of the two cystometrographic parameters were calculated. A typical tracing is shown in FIG. 2, where the effects of 3 mg/kg p.o. of COMPOUND A are shown. Before treatment, two cystometrograms with the same bladder volume capacity (BVC) were recorded. Cystometrographic recording performed 60 min after oral treatment with COMPOUND A resulted in two cystometrograms with a BVC values of 0.61 and 0.51 ml (35.6 and 13.3% increase, respectively). No substantial changes in MP were recorded.

The statistical significance of the differences in urodynamic parameter values was evaluated by Student's t test for paired data. Only changes showing a probability P<0.01 were considered to be significant.

B. Results:

The effects on urodynamic parameters in conscious rats after i.v. administration of different doses of COMPOUND A and the reference compounds are summarized in Tables 5 and 6.

TABLE 5

Effects on cystometrogram in conscious rats.
Data represent the mean ± S.E. values (ml) of bladder volume capacity (BVC), before and 15 min after i.v. injection of the compounds.

| COMPOUND Dose (µg/kg i.v.) | No. of rats | BVC before | after treat. | % of change |
|---|---|---|---|---|
| CONTROL vehicle | 12 | 0.50 ± 0.09 | 0.43 ± 0.06 | −17 |
| COMPOUND A | | | | |
| 100 | 8 | 0.65 ± 0.06 | 0.66 ± 0.08 | +4 |
| 300 | 9 | 0.47 ± 0.05 | 0.63 ± 0.06* | +32 |
| 1000 | 20 | 0.64 ± 0.05 | 0.83 ± 0.07* | +29 |
| 3000 | 10 | 0.48 ± 0.04 | 0.63 ± 0.05* | +32 |
| FLAVOXATE | | | | |
| 300 | 17 | 0.76 ± 0.11 | 0.87 ± 0.11 | +14 |
| 1000 | 14 | 0.88 ± 0.15 | 1.11 ± 0.16* | +26 |
| 3000 | 18 | 0.77 ± 0.08 | 1.07 ± 0.12* | +39 |
| OXYBUTYNIN | | | | |
| 100 | 13 | 0.82 ± 0.15 | 0.89 ± 0.18 | +9 |
| 300 | 12 | 0.83 ± 0.13 | 0.83 ± 0.12 | 0 |
| 1000 | 12 | 0.94 ± 0.19 | 1.00 ± 0.18 | +7 |
| COMPOUND Q[(A)] | | | | |
| 30 | 8 | 0.74 ± 0.09 | 0.78 ± 0.10 | +6 |
| 100 | 8 | 0.68 ± 0.10 | 0.76 ± 0.10 | +12 |
| 300 | 8 | 0.62 ± 0.06 | 0.61 ± 0.06 | −1 |

*= $p \leq 0.01$ (Student's t test for paired data)
A) = higher doses were not tested because of the high toxicity and low solubility of this compound.

TABLE 6

Effects on cystometrogram in conscious rats.
Data represent the mean values ± S.E. (mmHg) of micturition pressure (MP), before and 15 min after i.v. injection of the compounds.

| COMPOUND Dose (µg/kg i.v.) | No. of rats | MP before | after treat. | % change |
|---|---|---|---|---|
| CONTROL vehicle | 12 | 91.3 ± 9.2 | 87.9 ± 9.9 | −4 |
| COMPOUND A | | | | |
| 100 | 8 | 93.0 ± 8.3 | 83.8 ± 8.7 | −10 |
| 300 | 9 | 78.7 ± 5.8 | 70.0 ± 4.1 | −11 |
| 1000 | 20 | 104.6 ± 6.4 | 91.0 ± 6.3* | −13 |
| 3000 | 10 | 101.8 ± 10.9 | 81.5 ± 14.1 | −20 |
| FLAVOXATE | | | | |
| 300 | 17 | 89.2 ± 10.7 | 95.0 ± 10.9 | +7 |
| 1000 | 14 | 90.4 ± 10.7 | 0.1 ± 11.1 | −12 |
| 3000 | 18 | 72.6 ± 9.3 | 75.2 ± 9.5 | +4 |
| OXYBUTYNIN | | | | |
| 100 | 13 | 95.2 ± 9.2 | 77.4 ± 10.3* | −19 |
| 300 | 12 | 82.3 ± 8.7 | 50.5 ± 6.3* | −39 |
| 1000 | 12 | 110.9 ± 10.2 | 29.6 ± 5.6* | −73 |
| COMPOUND Q[(A)] | | | | |
| 30 | 8 | 99.4 ± 10.1 | 104.6 ± 9.7 | +5 |
| 100 | 8 | 93.8 ± 11.5 | 82.5 ± 9.2 | −12 |
| 300 | 8 | 86.6 ± 10.3 | 88.4 ± 11.8 | +2 |

*= $p \leq 0.01$ (Student's t test for paired data)
A) = higher doses were not tested because of the high toxicity and low solubility of this compound.

The administration of COMPOUND A induced constant and significant increases of the BVC. Flavoxate (1000–3000 µg/kg) also induced increases in BVC, and the differences between basal and after treatment values were statistically significant (Table 5).

Oxybutynin was inactive on BVC (Table 5), but induced very consistent, significant and dose-related reductions of MP (the approximate $ED_{50}$ value was 400 µg/kg), in contrast to COMPOUND A and flavoxate that were inactive on this parameter (Table 6). COMPOUND Q was devoid of significant effects on both parameters up to the highest administrable dose of 300 µg/kg.

The effects of these compounds after oral administration were also tested. The results are shown in Tables 7 and 8 below.

TABLE 7

Effects on cystometrogram in conscious rats.
Data represent the mean values ± S.E. (ml) of bladder volume capacity (BVC), before and 1 hr after oral administration of the compounds.

| COMPOUND Dose mg/kg p.o. | No. of rats | BVC before | after treat. | % change |
|---|---|---|---|---|
| CONTROL vehicle | 11 | 0.64 ± 0.10 | 0.73 ± 0.13 | +14 |
| COMPOUND A | | | | |
| 1 | 10 | 0.52 ± 0.07 | 0.60 ± 0.08 | +15 |
| 3 | 10 | 0.67 ± 0.07 | 0.91 ± 0.10* | +35 |
| 10 | 10 | 0.54 ± 0.06 | 0.73 ± 0.10* | +37 |
| OXYBUTYNIN | | | | |
| 1 | 8 | 0.56 ± 0.11 | 0.74 ± 0.11* | +31 |
| 3 | 8 | 0.54 ± 0.07 | 0.63 ± 0.13 | +18 |
| 10 | 8 | 0.55 ± 0.08 | 0.70 ± 0.11 | +27 |

TABLE 7-continued

Effects on cystometrogram in conscious rats.
Data represent the mean values ± S.E. (ml) of bladder volume capacity
(BVC), before and 1 hr after oral administration of the compounds.

| COMPOUND Dose mg/kg p.o. | No. of rats | BVC before | after treat. | % change |
|---|---|---|---|---|
| COMPOUND Q | | | | |
| 10 | 10 | 0.54 ± 0.08 | 0.46 ± 0.07 | −14 |
| 30 | 10 | 0.71 ± 0.09 | 0.60 ± 0.09 | −15 |

*= p ≦ 0.01 (Student's t test for paired data)

TABLE 8

Effects on cystometrogram in conscious rats.
Data represent the mean values ± S.E. (mmHg) of micturition pressure
(MP), before and 1 hr after oral administration of the compounds.

| COMPOUND Dose mg/kg p.o. | No. of rats | MP before | after treat. | % change |
|---|---|---|---|---|
| CONTROL vehicle | 11 | 84.1 ± 10.1 | 73.3 ± 11.0 | −13 |
| COMPOUND A | | | | |
| 1 | 10 | 96.0 ± 8.4 | 93.7 ± 7.2 | −2 |
| 3 | 10 | 112.5 ± 6.5 | 107.6 ± 9.2 | −4 |
| 10 | 10 | 90.2 ± 7.1 | 86.6 ± 7.6 | −4 |
| OXYBUTYNIN | | | | |
| 1 | 8 | 92.1 ± 13.3 | 77.3 ± 9.8 | −16 |
| 3 | 8 | 82.1 ± 5.1 | 42.1 ± 5.1* | −49 |
| 10 | 8 | 98.3 ± 9.0 | 31.8 ± 3.9* | −68 |
| COMPOUND Q | | | | |
| 10 | 10 | 106.1 ± 10.4 | 90.8 ± 12.5 | −14 |
| 30 | 10 | 105.1 ± 10.5 | 95.8 ± 15.3 | −9 |

*= p ≦ 0.01 (Student's t test for paired data)

COMPOUND A produced a significant increase of BVC after oral administration of 3 mg/kg, and no changes in MP values were detected. Oxybutynin caused a significant increase of the BVC after oral administration at the lowest utilized dose (1 mg/kg), and produced a dose-related reduction of the MP values that was consistent and significant with 3 and 10 mg/kg dose-levels (approximate $ED_{50}$ value was 4 mg/kg). COMPOUND Q was inactive after oral administration at doses up to 30 mg/kg, a dose 10-fold higher than the minimal effective dose of COMPOUND A.

These results were consistent with those obtained in anesthetized rats as described in Example 8 above. COMPOUND A was found to be active in increasing the BVC without affecting bladder contractility (MP), in contrast to oxybutynin. COMPOUND A was also found to be active after both i.v. and oral administration, in contrast to COMPOUND Q which was inactive after i.v. or oral administration of doses up to 10-fold higher than those used for COMPOUND A.

The above results show that compounds endowed with antagonistic activity at pre- and post-synaptic $5\text{-}HT_{1A}$ receptors and devoid of significant affinity for the $\alpha_1$-adrenergic receptors are unexpectedly endowed with a potent pharmacological activity on the lower urinary tract. In particular, these compounds are able to inhibit the micturition reflex and to increase the period between micturition without impairing the capability of detrusor to have effective voidings once the micturition threshold has been reached. An additional advantage of these compounds is that (unlike anticholinergics) they do not reduce the efficiency of micturition. Thus, the compounds of the invention avoid impairment of bladder contractile force and the consequent increase in residual urine. Hence these compounds can be used effectively in the treatment of dysuria, urinary frequency, urgency, incontinence and enuresis, without the risk of elevated residual volume of urine in the bladder.

We claim:

1. A method for treating neuromuscular dysfunction of the lower urinary tract in a mammal in need of such treatment, said method comprising administering to said mammal an effective amount for treating said dysfunction of a $5\text{-}HT_{1A}$ receptor antagonist compound selected from the group consisting of compounds having Formula I:

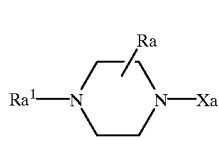

(I)

wherein:

Ra is selected from the group consisting of hydrogen, and lower alkyl;

$Ra^1$ is selected from the group consisting of aryl, nitrogen-containing heteroaryl, and bicyclic heteroaryl; and Xa is selected from the group consisting of

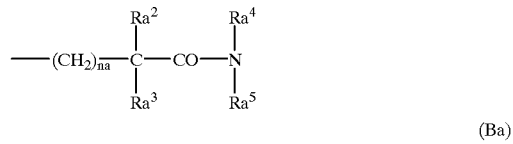

(Aa)

(Ba)

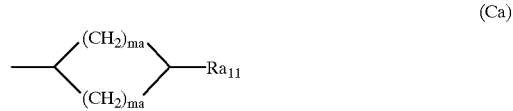

(Ca)

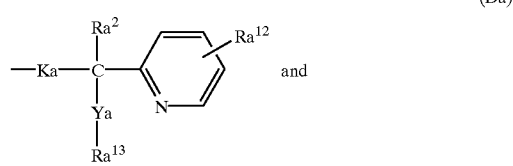

(Da)

and

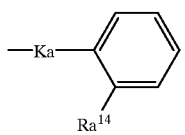

(Ea)

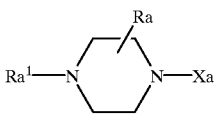

(I)

wherein na is 1 or 2; ma is 1, 2, or 3;

$Ra^2$ and $Ra^4$ are independently selected from the group consisting of hydrogen and lower alkyl;

$Ra^3$ is selected from the group consisting of aryl and aryl(lower)alkyl;

$Ra^5$ is selected from the group consisting of hydrogen, lower alkyl, cycloalkyl, and cycloalkyl(lower)alkyl; or $Ra^4$ and $Ra^5$ taken together with the nitrogen atom to which they are attached can form, a ring, such as, for example, an azetidino, pyrrolidino, piperidino, hexahydroazepino, morpholino, or piperazino ring; said ring can optionally be substituted by lower alkyl, aryl, or aryl(lower)alkyl;

Ka is a $C_2$–$C_4$ alkylene chain which can be optionally substituted by one or more lower alkyl groups;

$Ra^6$ is selected from the group consisting of a monocyclic heteroaryl radical and a bicyclic heteroaryl radical;

$Ra^7$ is selected from the group consisting of hydrogen, lower alkyl, cycloalkyl, cycloalkenyl, cycloalkyl (lower)alkyl, aryl, aryl(lower)alkyl, heteroaryl, heteroaryl(lower)alkyl, —$NRa^8Ra^9$, and —O—$Ra^{10}$;

wherein $Ra^8$ is selected from the group consisting of hydrogen, lower alkyl, aryl, and aryl(lower)alkyl;

$Ra^9$ is selected from the group consisting of hydrogen, lower alkyl, —CO—(lower)alkyl, aryl, —CO—aryl, aryl(lower)alkyl, cycloalkyl, and cycloalkyl(lower) alkyl; or $Ra^8$ and $Ra^9$ taken together with the nitrogen atom to which they are attached can form a saturated heterocyclic ring which optionally contains additional hetero atoms; and $Ra^{10}$ is selected from the group consisting of lower alkyl, cycloalkyl, cycloalkyl(lower)alkyl, aryl, aryl(lower) alkyl, heteroaryl, and heteroaryl(lower)alkyl;

$Ra^{11}$ is selected from the group consisting of aryl, and heteroaryl containing at least one nitrogen atom; and $Ra^{12}$ is hydrogen or lower alkyl;

$Ra^{13}$ is hydrogen, alkyl, cycloalkyl or cycloakyl(lower) alkyl; and $Ra^4$ is aryl; and Ya is selected from the group consisting of carbonyl, alkylene, hydroxymethylene, hydroxyalkylene, hydroxycycloalkylene, and —$S(O)_{na}$; where na=0–2; or stereoisomers, pharmaceutically acceptable acid addition salts, hydrates or solvates of the foregoing.

2. The method of claim 1, wherein said compound has the formula or a pharmaceutically acceptable acid addition salt, hydrate or solvate thereof.

3. The method of claim 2, wherein $Ra^1$ is aryl, 1-naphthyl, or 4-indolyl.

4. The method of claim 3, wherein said aryl is a phenyl radical substituted in the ortho position.

5. The method of claim 4, wherein said phenyl radical is o-methoxyphenyl.

6. The method of claim 1, wherein $Ra^1$ is alkoxy-substituted aryl or a nitrogen-containing heteroaryl;

Xa is structure Ba, where Ka is an alkylene chain having 2 carbons, $Ra^6$ is pyridyl, and $Ra^7$ is hydrogen or cycloalkyl; and Ra is hydrogen.

7. The method according to claim 1, wherein the active agent is a compound selected from the group consisting of:
2,3,4,5,6,7-hexahydro-1-{4-[1-[4-(2-methoxyphenyl)-piperazin-yl]]-3-phenyl}butanoyl-1 H-azepine,
2,3,4,5,6,7-hexahydro-1-{4-[4-(2-methoxyphenyl)-piperazin-1-yl]-2-phenyl}butanoyl-1H-azepine,
N-{2-[4-(2-methoxyphenyl)-1-piperazinyl]ethyl}-N-(2-pyridinyl)-cyclohexanecarboxamide (Compound A),
1-[2-[(2-Pyridylamino)ethyl]-4-(2-methoxyphenyl) piperazine (Compound B),
N-[2-[4-(4-Indolyl)-1-piperazinyl]ethyl]-N-(2-pyridyl) cyclohexanecarboxamide (Compound C), and
1-[2-[(2-Pyridylamino)ethyl]-4-(4-indolyl)piperazine (Compound D),
1-[2-(2-biphenyl)ethyl]-4-(2-methoxyphenyl)piperazine
or a pharmaceutically acceptable acid addition salt, hydrate or solvate thereof.

8. The method of claim 1, wherein the compound is an (S)-enantiomer.

9. The method of claim 1, wherein the compound is an (R)-enantiomer.

10. The method of claim 1, wherein said dysfunction is selected from the group consisting of dysuria, urinary incontinence, and enuresis.

11. The method of claim 1, wherein said administering is achieved using a route selected from the group consisting of oral, enteral, intravenous, intramuscular, subcutaneous, transmucosal, transdermal, and by-inhalation routes.

12. The method of claim 1, wherein said compound is administered to said mammal in an amount of between about 0.01 and 25 mg/kg/day.

13. The method of claim 12, wherein said amount is between about 0.2 and about 5 mg/kg/day.

14. The method of claim 12, wherein said amount is administered in an amount from about 50 to 250 mg/day.

15. The method of claim 14, wherein the amount of said compound is about 200 mg/day.

16. The method of claim 12, wherein said amount is administered in an amount from about 30 to about 90 mg/day.

17. The method of claim 16, wherein the amount of said compound is about 60 mg/day.

18. The method of claim 1, wherein said compound is N-[2-[4-Indolyl)-1-piperazinyl]ethyl]-N-(2-pyridyl) cyclohexanecarboxamide.

19. The method of claim 1, wherein said compound is N-[2-[4(2-Methoxyphenyl)-1-piperazinyl]ethyl]-N-(2-pyridinyl)cyclohexanecarboxamide.

20. The method of claim 1, wherein said compound exhibits 5-$HT_{1A}$ receptor antagonist activity at both pre-synaptic and post-synaptic 5-$HT_{1A}$ receptor sites.

21. A method for treating neuromuscular dysfunction of the lower urinary tract in a mammal in need of such treatment, said method comprising administering to said mammal the compound N-[2-[4-(4-Indolyl)-1-piperazinyl] ethyl]-N-(2-pyridyl)cyclohexanecarboxamide, in an amount and for a time sufficient to treat said dysfunction.

22. The method of claim 21, wherein said dysfunction is selected from the group consisting of dysuria, urinary incontinence, and enuresis.

23. The method of claim 21, wherein said administering is achieved using a route selected from the group consisting of oral, enteral, intravenous, intramuscular, subcutaneous, transmucosal, transdermal, and by-inhalation routes.

24. The method of claim 21, wherein said compound is administered to said mammal in an amount of between about 0.01 and 25 mg/kg/day.

25. The method of claim 24, wherein said amount is between about 0.2 and about 5 mg/kg/day.

26. The method of claim 21, wherein said amount is about 60 mg/day.

27. The method of claim 21, wherein said compound exhibits 5-$HT_{1A}$ receptor antagonist activity at both pre-synaptic and post-synaptic 5-$HT_{1A}$ receptor sites.

28. A method for treating neuromuscular dysfunction of the lower urinary tract in a mammal in need of such treatment, said method comprising administering to said mammal N-[2-[4-(2-Methoxyphenyl-1-piperazinyl]ethyl]-N-(2-pyridinyl)cyclohexanecarboxamide, in an amount and for a time sufficient to treat said dysfunction.

29. The method of claim 28, wherein said dysfunction is selected from the group consisting of dysuria, urinary incontinence, and enuresis.

30. The method of claim 28, wherein said administering is achieved using a route selected from the group consisting of oral, enteral, intravenous, intramuscular, subcutaneous, transmucosal, transdermal, and by-inhalation routes.

31. The method of claim 28, wherein said compound is administered to said mammal in an amount of between about 0.01 and 25 mg/kg/day.

32. The method of claim 28, wherein said amount is between about 0.2 and about 5 mg/kg/day.

33. The method of claim 28, wherein said amount is about 200 mg/day.

34. A method for treatment of nueromuscular disorders of the lower urinary tract, said method comprising administration to a mammal in need of said treatment, a pharmaceutical composition comprising a compound selected from the group consisting of 2,3,4,5,6,7-hexahydro-1-{4-[1-[4-(2-methoxyphenyl)-piperazin-yl]]-3-phenyl}butanoyl-1H-azepine, 2,3,4,5,6,7-hexahydro-1-{4-[4-(2-methoxyphenyl)-piperazin-1-yl]-2-phenyl }butanoyl-1H-azepine, N-{2-[4-(2-methoxyphenyl)-1-piperazinyl]ethyl}-N-(2-pyridinyl)cyclo-hexanecarboxamide (COMPOUND A), 1-[2-[(2-Pyridylamino)ethyl]-4-(2-methoxyphenyl) piperazine (Compound B), N-[2-[4-(4-Indolyl)-1-piperazinyl]ethyl]-N-(2-pyridyl) cyclohexanecarboxamide (COMPOUND C), 1-[2-[(2-Pyridylamino)ethyl]-4-(4-indolyl)piperazine (Compound D), 1-[2-(2-biphenyl)ethyl]-4-(2-methoxyphenyl)piperazine or a pharmaceutically acceptable acid addition salt, hydrate or solvate thereof.

35. The method of claim 1, wherein said 5-$HT_{1A}$ receptor antagonist compound (1) binds to a 5-$HT_{1A}$ receptor with an affinity of at least about $10^{-7}$ M and binds to a 5-$HT_{1A}$ receptor with an affinity at least about 10-fold stronger than the affinity with which the compound binds to a α1-adrenergic receptor; and (2) inhibits both the frequency of rhythmic bladder voidings and the frequency of voiding contractions.

* * * * *